(12) United States Patent
Jamiolkowski et al.

(10) Patent No.: US 10,058,637 B2
(45) Date of Patent: *Aug. 28, 2018

(54) ABSORBABLE POLYMERIC BLEND COMPOSITIONS WITH PRECISELY CONTROLLABLE ABSORPTION RATES, PROCESSING METHODS, AND DIMENSIONALLY STABLE MEDICAL DEVICES THEREFROM

(71) Applicant: Ethicon, Inc., Somerville, NJ (US)

(72) Inventors: Dennis D. Jamiolkowski, Long Valley, NJ (US); Daniel Steiger, Basking Ridge, NJ (US); Brian M. Kelly, Ringoes, NJ (US); Christopher DeFelice, Springfield, NJ (US); Sasa Andjelic, Nanuet, NY (US); Modesto Erneta, Princeton Junction, NJ (US)

(73) Assignee: Ethicon, LLC, San Lorenzo, PR (US)

( * ) Notice: Subject to any disclaimer, the term of this patent is extended or adjusted under 35 U.S.C. 154(b) by 81 days.

This patent is subject to a terminal disclaimer.

(21) Appl. No.: 14/548,536

(22) Filed: Nov. 20, 2014

(65) Prior Publication Data

US 2015/0148496 A1  May 28, 2015

Related U.S. Application Data

(60) Provisional application No. 61/909,419, filed on Nov. 27, 2013.

(51) Int. Cl.
| | |
|---|---|
| A61L 27/26 | (2006.01) |
| A61L 27/58 | (2006.01) |
| C08L 67/04 | (2006.01) |
| A61L 31/04 | (2006.01) |
| A61L 31/14 | (2006.01) |
| A61B 17/064 | (2006.01) |
| A61L 17/10 | (2006.01) |
| A61B 17/06 | (2006.01) |
| A61B 17/00 | (2006.01) |

(52) U.S. Cl.
CPC .......... *A61L 31/041* (2013.01); *A61B 17/064* (2013.01); *A61L 17/105* (2013.01); *A61L 27/26* (2013.01); *A61L 27/58* (2013.01); *A61L 31/148* (2013.01); *C08L 67/04* (2013.01); *A61B 17/06166* (2013.01); *A61B 2017/00004* (2013.01); *C08L 2205/03* (2013.01)

(58) Field of Classification Search
None
See application file for complete search history.

(56) References Cited

U.S. PATENT DOCUMENTS

| | | | |
|---|---|---|---|
| 4,646,741 A | 3/1987 | Smith | |
| 5,705,181 A | 1/1998 | Cooper et al. | |
| 7,524,891 B2 | 4/2009 | Rose et al. | |
| 8,354,476 B2 * | 1/2013 | Hanes | A61K 47/48192 |
| | | | 525/327.4 |
| 2005/0048099 A1* | 3/2005 | Shiah | A61K 9/0051 |
| | | | 424/428 |
| 2007/0149640 A1 | 6/2007 | Andjelic et al. | |
| 2009/0118241 A1 | 5/2009 | Andjelic et al. | |
| 2009/0274742 A1 | 11/2009 | Brown | |
| 2012/0071566 A1 | 3/2012 | Kelly et al. | |

FOREIGN PATENT DOCUMENTS

| | | |
|---|---|---|
| EP | 0853949 | 4/2003 |
| WO | WO 94/06856 | 3/1994 |
| WO | WO 2009/148581 | 12/2009 |

* cited by examiner

*Primary Examiner* — David J Blanchard
*Assistant Examiner* — Sarah J Chickos
(74) *Attorney, Agent, or Firm* — E. Richard Skula

(57) ABSTRACT

Novel absorbable polymeric blends are disclosed. The blends have a first absorbable polymer type that is a polylactide polymer or a copolymer of lactide and glycolide and a second absorbable polymer type that is poly(p-dioxanone), wherein the first absorbable polymer type or the second absorbable polymer type or the first absorbable polymer type and the second absorbable polymer type additionally comprise a first polymeric component and a second polymeric component. The first polymeric component has a higher weight average molecular weight than the second polymeric component and at least one of said components is at least partially end-capped by a carboxylic acid. The novel polymeric blends are useful for manufacturing medical devices having dimensional stability, having engineered degradation and breaking strength retention in vivo. Also disclosed are novel absorbable medical devices made from these novel polymer blends, as well as novel methods of manufacture.

24 Claims, 5 Drawing Sheets

ABSORBABLE POLYMERIC BLEND COMPOSITIONS WITH PRECISELY CONTROLLABLE ABSORPTION RATES, PROCESSING METHODS, AND DIMENSIONALLY STABLE MEDICAL DEVICES THEREFROM

FIELD OF THE INVENTION

The field of art to which this invention relates is absorbable polymers, in particular, absorbable polymer blends useful for manufacturing medical devices.

BACKGROUND OF THE INVENTION

Absorbable polymers and medical devices made from such polymers are known in the art. Conventional absorbable polymers include polylactic acid, poly(p-dioxanone), polyglycolic acid, co-polymers of lactide, glycolide, p-dioxanone, trimethylene carbonate, ε-caprolactone, in various combinations, etc. The chemistry of absorbable polymers is designed such that the polymers breakdown in vivo, for example by hydrolysis, and the byproducts are metabolized or otherwise excreted from the patient's body. The advantages of utilizing implantable medical devices made from absorbable polymers are numerous and include, for example, eliminating the need for additional surgeries to remove an implant after it serves its function. In the case of a wound closure function, when a "temporary presence" of the implant is desired, ideally support can be provided until the tissue heals.

Absorbable is meant to be a generic term, which may also include bioabsorbable resorbable, bioresorbable, degradable or biodegradable.

The absorbable polymers conventionally used to manufacture medical devices have been on occasion polymeric blends of absorbable polymers and co-polymers engineered to provide specific characteristics and properties to the manufactured medical device, including absorption rates, mechanical property (e.g., stiffness, breaking strength, etc.), mechanical property retention post-implantation, and dimensional stability, etc.

There are many conventional processes used to manufacture medical devices from absorbable polymers and polymer blends. The processes include injection molding, solvent casting, extrusion, machining, cutting and various combinations and equivalents. A particularly useful and common manufacturing method is thermal forming using conventional injection molding processes and extrusion processes.

The retention of mechanical properties post-implantation is often a very important feature of an absorbable medical device. The device must retain mechanical integrity until the tissue has healed sufficiently. In some bodily tissues, healing occurs more slowly, requiring an extended retention of mechanical integrity. This is often associated with tissue that has poor vascularization. Likewise there are other situations in which a given patient may be prone to poor healing: e.g., the diabetic patient. There are however many situations in which rapid healing occurs, which require the use of fast absorbing medical devices such as sutures or other fixation devices; this is often associated with excellent tissue vascularization. Examples of where such fast absorbing sutures or other fast absorbing fixation devices can be used include certain pediatric surgeries, oral surgery, repair of the peritoneum after an episiotomy, and superficial wound closures.

When rapid healing occurs, the mechanical retention profile of the medical device can reflect a more rapid loss in properties. Concomitant with this is the rate of absorption (absorption, bioabsorption, or resorption), that is, the time required for the medical device to disappear from the surgical site.

One method that has been exploited to achieve the rapid loss of mechanical properties in absorbable medical devices is the use of pre-hydrolysis and/or gamma irradiation. For instance Hinsch et al., in EP 0 853 949 B 1, describe a process for reducing the resorption period of hydrolyzable surgical suture material, wherein the surgical suture material is incubated in a hydrolysis buffer, having an index of pH in the range from 4 to 10, for a period in the range from 10 hours to 100 hours at a temperature in the range from 30° C. to 65° C.

In order to shorten the absorption period of absorbable suture material it is also known to irradiate the suture material during the manufacture, e.g., by means of Co-60 gamma irradiation. Such an irradiation process produces defects in the polymer structure of the suture material, resulting in an accelerated decrease of the tensile strength and a shortened absorption period in vivo after implantation of the suture material. The use of gamma irradiation in a manufacturing environment in order to reliably adjust in vivo absorption times and control post-implantation mechanical property loss is often difficult due to a variety of reasons. These reasons include the high precision required, and, the unintended damage to other important properties such as discoloration.

It is well known, however, that such treatments of pre-hydrolysis and gamma irradiation may have a negative effect on the mechanical properties of the device. Consequently, and for example, sutures that are touted as fast absorbing are often lower in initial strength than their standard absorbing suture counterparts.

In certain surgical procedures, the mechanical properties, particularly the tensile strength, of the wound closure devices are clinically very important; in these wound closure devices, such as sutures, high strength is generally preferred. Commercially available braided fast absorbing suture sold by ETHICON, Inc., Somerville, N.J. 08876, and known as VICRYL RAPIDE™ (Polyglactin 910) Suture exhibits a tensile strength of about 60 percent of the standard absorbing counterpart, Coated VICRYL™ (Polyglactin 910) Suture. In other surgical procedures, a particularly important mechanical property of the medical device is stiffness, which might come into play during tissue penetration, etc. A further need is to provide devices exhibiting dimensional stability during sterilization, transportation, and storage.

There is a continuing need in this art for novel, dimensionally stable medical devices that lose their mechanical properties quickly and are absorbed rapidly, but which still provide high initial mechanical properties approaching those exhibited by their standard absorbing counterparts.

There have been attempts in the prior art to address the problem of rapid absorption. Rose and Hardwick in U.S. Pat. No. 7,524,891 describe the addition of certain carboxylic acids and their derivatives and anhydrides to poly(lactic acid) to make homogeneous blends, which exhibit a more rapid absorption. It should be noted that that they limit the amount of the additive to 10 weight percent. They clearly describe a system in which the additive is admixed throughout and is not reactive with the poly(lactic acid) so as to create a derivative.

There have been attempts in the prior art to address the problem of improved strength.

For instance, Brown in U.S. Patent Application Publication No. 2009/0274742 A1, entitled "Multimodal High Strength Devices And Composites", (hereinafter referred to as "'742") discloses an oriented implantable biodegradable multimodal device comprising a blend of a first polymer component having a first molecular weight together with at least a second polymer component having a molecular weight which is less than that of the first component, wherein polymer components within the blend are in uniaxial, biaxial or triaxial orientation. Brown speaks of achieving higher mechanical properties in blends of high molecular weight polylactide (e.g., IV=4.51 dL/g) with much lower molecular weight versions of this polymer (Mw=5,040 Da, Mn=3,827 Da), but only shows an increase in modulus and no increase in maximum stress. Additionally, Brown in '742 mentions a faster rate of absorption as compared to the high molecular weight polylactide when an additive is admixed in an amount of not more than 10% by weight of the polymer components.

A bimodal absorbable polymer composition is disclosed in U.S. Patent Application Publication No. US 2007/0149640 A1. The composition includes a first amount of an absorbable polymer polymerized so as to have a first molecular weight distribution and a second amount of said absorbable polymer polymerized so as to have a second molecular weight distribution having a weight average molecular weight between about 20,000 to about 50,000 Daltons. The weight average molecular weight ratio of said first molecular weight distribution to said second molecular weight distribution is at least about two to one, wherein a substantially homogeneous blend of said first and second amounts of said absorbable polymer is formed in a ratio of between about 50/50 to about 95/5 weight/weight percent. Also disclosed are a medical device and a method of making a medical device.

In U.S. Patent Application Publication No. US 2009/0118241 A1, a bimodal absorbable polymer composition is disclosed. The composition includes a first amount of an absorbable polymer polymerized so as to have a first molecular weight distribution and a second amount of said absorbable polymer polymerized so as to have a second molecular weight distribution having a weight average molecular weight between about 10,000 to about 50,000 Daltons. The weight average molecular weight ratio of said first molecular weight distribution to said second molecular weight distribution is at least about two to one, wherein a substantially homogeneous blend of said first and second amounts of said absorbable polymer is formed in a ratio of between about 50/50 to about 95/5 weight/weight percent. Also disclosed are a medical device, a method of making a medical device and a method of melt blowing a semi-crystalline polymer blend.

Even though such polymer blends are known, there is a continuing need in this art for novel absorbable polymeric materials having precisely controllable absorption rates, that provide a medical device with improved characteristics including stiffness, retained strength in vivo (in situ), dimensional stability, absorbability in vivo, and manufacturability; there is a particular need for accelerated absorption and accelerated mechanical property loss post-implantation while still exhibiting high initial mechanical properties.

As mentioned earlier, absorbable polymers and medical devices made from such polymers are known in the art. Conventional absorbable polymers include polylactic acid, poly(p-dioxanone), polyglycolic acid, copolymers of lactide, glycolide, p-dioxanone, trimethylene carbonate, ε-caprolactone, in various combinations, etc. The absorbable polymers are designed to have a chemistry such that the polymers breakdown in vivo and are either metabolized or otherwise broken down, for example by hydrolysis, and excreted from the patient's body. The advantages of utilizing implantable medical devices made from absorbable polymers are numerous and include, for example, eliminating the need for additional surgeries to remove an implant after it serves its function. Ideally when a "temporary presence" of the implant is desired, support can be provided until the tissue heals.

The absorbable polymers used to manufacture medical devices have been on occasion polymeric blends of absorbable polymers and copolymers engineered to provide specific characteristics and properties to the manufactured medical device, including absorption rates, breaking strength retention, and dimensional stability, etc.

There are many conventional processes used to manufacture medical devices from absorbable polymers and polymer blends. The processes include injection molding, solvent casting, extrusion, machining, cutting and various combinations and equivalents. A particularly useful and common manufacturing method is thermal forming using conventional injection molding processes. It is known in this art that manufacturing processes such as thermal injection molding may result in molded parts that have inferior properties, especially, for example, unacceptable dimensional stability, mechanical properties, and retention of mechanical properties over time post-implantation. There are a number of reasons for diminished dimensional stability. They include the presence of residual stresses induced during the manufacturing process. Another reason for a lack of dimensional stability is if at least one of the polymeric components possesses too low of a glass transition temperature, especially if the polymeric component does not easily crystallize after molding.

Therefore, there is a need in this art for novel absorbable polymer blends that can be used in thermal injection molding processes, and other conventional processes, to manufacture absorbable medical devices having superior mechanical properties, such as stiffness and strength, breaking strength retention post-implantation, excellent absorption, manufacturability, and superior dimensional stability.

It is known when using thermal injection molding processes that process conditions and design elements that reduce shear stress during cavity filling will typically help to reduce flow-induced residual stress. Likewise, those conditions that promote sufficient packing and uniform mold cooling will also typically tend to reduce thermally-induced residual stress. It is often very difficult, if not nearly impossible to completely eliminate residual stress in injection molded parts. Some approaches that have been employed include: (1) attempting to crystallize the part while still in the mold to increase the mechanical rigidity to resist distortion; and, (2) employing resins having a high glass transition temperature ($T_g$).

This later case describes the situation wherein chain mobility is only reached at much higher temperatures, thus protecting the part at the moderate temperatures that the part might be expected to endure during ethylene oxide (EO) sterilization, shipping, and storage. Materials possessing high glass transition temperatures may not necessarily possess other characteristics that are desirable such as absorbability. Residual stresses are believed to be the main cause of part shrinkage and warpage. Parts may warp or distort dimensionally upon ejection from the mold during the injection molding cycle, or upon exposure to elevated temperatures, encountered during normal storage or shipping of the product.

There have been attempts in the prior art to address the problem of lack of dimensional stability in medical devices thermally formed from melt blended absorbable polymers. Smith, U.S. Pat. No. 4,646,741, discloses a melt blend of a lactide/glycolide copolymer and poly(p-dioxanone) used to make surgical clips and two-piece staples. The melt blends of Smith provide molded articles possessing dimensional stability; Smith requires that the amount of poly(p-dioxanone) in the blend be greater than 25 weight percent and teaches away from lower amounts. The polymer blends of Smith have disadvantages associated with their use to manufacture medical devices, including: limited stiffness or Young's modulus, shorter retention of mechanical properties upon implantation, greater sensitivity to moisture limiting the allowable open storage time during manufacture, and, although difficult to quantify, more difficult thermal processing.

As mentioned previously, residual stresses are believed to be the main cause of part shrinkage and warpage. It is known that flow-induced residual stresses may have an effect upon a thermally molded polymeric medical device. Unstressed, long-chain polymer molecules tend to conform to a random-coil state of equilibrium at temperatures higher than the melt temperature (i.e., in a molten state). During thermal processing (e.g., injection molding), the molecules orient in the direction of flow, as the polymer is sheared and elongated. Solidification usually occurs before the polymer molecules are fully relaxed to their state of equilibrium and some molecular orientation is then locked within the molded part. This type of frozen-in, stressed state is often referred to as flow-induced residual stress. Anisotropic, non-uniform shrinkage and mechanical properties in the directions parallel and perpendicular to the direction of flow are introduced because of the stretched molecular structure.

Cooling can also result in residual stresses. For example, variation in the cooling rate from the mold wall to its center can cause thermally-induced residual stress. Furthermore, asymmetrical thermally-induced residual stress can occur if the cooling rate of the two surfaces is unbalanced. Such unbalanced cooling will result in an asymmetric tension-compression pattern across the part, causing a bending moment that tends to cause part warpage. Consequently, parts with non-uniform thickness or poorly cooled areas are prone to unbalanced cooling, and thus to residual thermal stresses. For moderately complex parts, the thermally-induced residual stress distribution is further complicated by non-uniform wall thickness, mold cooling, and mold constraints.

It should be noted that a common, conventional method of sterilization is exposure to ethylene oxide gas in a sterilization process cycle. Absorbable polymeric devices are frequently sterilized by exposure to ethylene oxide (EO) gas. EO can act as a plasticizer of lactone-based polyesters, such as lactide-glycolide copolymers, and can lower the $T_g$ slightly; this may result in 'shrinkage' and/or 'warpage' of an injection-molded part, especially when exposed to temperatures higher than the Tg. This adds additional processing and handling challenges when using lactide-glycolide polymeric materials for absorbable medical devices. It should be noted that an EO sterilization process not only exposes the part to EO gas, it also exposes the part to elevated temperatures. Because EO can act as a plasticizer of synthetic absorbable polyesters, the problems of shrinkage and warpage and general dimensional instability are often exacerbated for parts exposed to an EO sterilization process cycle.

There are a number of processing methods conventionally used to reduce or eliminate shear stresses during thermal forming processing. Process conditions and design elements that reduce shear stress during cavity filling will help to reduce flow-induced residual stress. Polymeric parts are often heat treated (thermally annealed) to alter their performance characteristics. The reason for the heat treatment processing is to mature the morphological development, for example crystallization and/or stress relaxation. If done successfully, the resulting part may exhibit better dimensional stability and may exhibit better mechanical properties.

Injection molded parts ejected from the injection molding machine that are not already distorted, can be cooled/quenched to room temperature and may appear to be dimensionally sound. Stresses, however, are usually still present and can drive distortion any time the polymer chains are allowed to mobilize. As previously described, this can happen with an increase in temperature or exposure to a plasticizer such as EO gas. In order to overcome this potential driving force for dimensional distortion, a number of strategies have been taken; these include (thermal) annealing.

If the part can be dimensionally constrained, thermal annealing can be employed towards two goals: one is to attempt to reduce the amount of molecular orientation in the polymer chains, also known as stress reduction; and, another is to increase the crystallinity in the part to increase the mechanical rigidity to resist distortion.

With some polymers that readily crystallize, one might be able to crystallize the part while it is still in the mold, but this is an unusual situation. Here the mold cavity not only acts to define the shape of the part, it can act to restrain the shape of the part during the crystallization process. With more-difficult-to-crystallize polymers, the cycle time becomes prohibitively long, and the injection molding process becomes impractical. Thus, the part needs to be ejected from the mold before complete polymer morphology development takes place.

Injection molded parts prepared from semi-crystalline polymers can often be annealed by thermal treatment to increase their crystallinity level and complete their polymer morphology development. Often the parts must be physically constrained to avoid the distortion one is attempting to avoid. Once crystallized, the part has increased mechanical rigidity to resist distortion if exposed to normally distorting conditions. Providing suitable physical constraint is often difficult, as it is often labor intensive and economically taxing.

Annealing the ejected part without need for physical constraint is preferred; however, what often happens is that the part distorts during the annealing process rendering the part unacceptable for many needs.

It is known in the industry to anneal parts to reduce molded-in-stresses by thermal relaxation. The time and temperature required to relieve stress varies but must often be done below the $T_g$ to avoid gross distortion. Even then the results can vary greatly. It is more difficult to reduce stress levels, without causing distortion, in higher molecular weight resins. It would be relatively easy to reduce molded-in-stresses by thermal relaxation in low molecular weight, high flow polyesters, as compared to higher molecular weight polyesters.

Regarding the molecular weight of the polymer blend, higher molecular weight usually develops higher stress levels and requires longer times/higher temperatures for stress relaxation. Although this is the case, higher molecular weight is often needed to achieve high mechanical properties and biological performance. This situation often presents a problem for the device manufacturer.

In order to impart more crystallinity to increase mechanical rigidity to better resist distortion, or to reduce molecular orientation in order to lower the driving force for distortion, the parts would ideally be processed by thermal treatment (annealing) at a temperature which does not cause distortion. Unfortunately, due to the nature of the synthetic absorbable polyesters commonly employed, this treatment often needs to be above their glass transition temperature where distortion is nearly impossible to avoid.

Consider for example, polylactide homopolymeric or poly(lactide-co-glycolide) copolymeric devices. The stressed polymer chains of these injection-molded parts will tend to relax and return to their natural state ("random three-dimensional coils") when heated to or above their glass transition temperatures. This will be observed as warpage, shrinkage or general dimensional deformation. It is a general practice in the industry when producing molded polylactide-based parts, not to anneal them because of this potential deformation. These as-molded polylactide parts are of very low crystallinity, if not outright amorphous or non-crystalline, and will then tend to deform if exposed to temperatures at or above their respective glass transition temperatures. It would be advantageous to be able to anneal such parts to induce crystallinity so that they may develop the high rigidity to remain dimensionally stable under conditions normally encountered during EO sterilization, shipping, and storage.

There are medical applications that require the medical device to display sufficient column strength such as in the case of an implantable staple or a tack. Clearly, for a device having such a requirement with a smaller cross-sectional area, the polymer from which it was formed must be inherently stiff if the tack is to function properly for the intended application.

To achieve higher stiffness in a melt blend of a lactide/glycolide copolymer and poly(p-dioxanone), for example, one needs to minimize the amount of poly(p-dioxanone). Contrary to what Smith teaches as discussed above, it has been found that dimensional stability can be achieved in parts molded from a blend of polylactide, or a lactide-rich copolymer, and poly(p-dioxanone) in which the levels of poly(p-dioxanone) are lower than 25 weight percent. The addition of the poly(p-dioxanone), even at these low levels, enhances the ability to achieve dimensional stability in the final part.

Even though such polymer blends are known, there is a continuing need in this art for novel absorbable polymeric materials that provide a medical device with improved characteristics including high initial mechanical properties (e.g., stiffness), accelerated loss of mechanical properties post-implantation, accelerated absorbability in vivo, dimensional stability, and manufacturability, along with a need for novel medical devices made from such polymeric materials, and novel methods of manufacturing medical devices from such polymeric materials.

SUMMARY OF THE INVENTION

It is an object of the present invention to provide novel absorbable polymer blends that can be used in manufacturing processes to produce novel absorbable medical devices and medical device components by melt processes, such as extrusion or injection molding.

Accordingly, novel absorbable polymer blends are disclosed. The absorbable blends have a first absorbable polymer type and a second absorbable polymer type. The first absorbable polymer type comprises at least 50 weight percent of the blend and further comprises about 100 mole percent to about 70 mole percent polymerized lactide and about 0 mole percent to about 30 mole percent polymerized glycolide, while the second polymer type comprises poly(p-dioxanone). The maximum weight percent of poly(p-dioxanone) in the blend is 50 weight percent while the minimum weight percent of poly(p-dioxanone) in the blend is sufficient so that the polymer blend effectively provides dimensional stability to a manufactured article. Wherein further, the first absorbable polymer type or the second absorbable polymer type or the first absorbable polymer type and the second absorbable polymer type comprise a first polymeric component and a second polymeric component. The first polymeric component has a higher weight average molecular weight than the second polymeric component, and, at least one of said components is at least partially end-capped by a carboxylic acid.

Another aspect of the present invention is an absorbable polymer blend. The blend has a first absorbable polymer type and a second absorbable polymer type. The first absorbable polymer type comprises at least 50 weight percent of the blend and further comprises about 100 mole percent to about 70 mole percent polymerized lactide and about 0 mole percent to about 30 mole percent polymerized glycolide; and, the second polymer type comprises poly(p-dioxanone). The maximum weight percent of poly(p-dioxanone) in the blend is 50 weight percent and the minimum weight percent of poly(p-dioxanone) in the blend is sufficient so that the polymer blend effectively provides dimensional stability to a manufactured article. Additionally, the first absorbable polymer type or the second absorbable polymer type or the first absorbable polymer type and the second absorbable polymer type comprise a polymeric component and an oligomeric component. The polymeric component has a higher weight average molecular weight than the oligomeric component and at least one of said components is at least partially end-capped by a carboxylic acid. The minimum weight percent of poly(p-dioxanone) in the blend depends upon the molar amount of polymerized lactide in the first absorbable polymer type and is calculated by the expression:

$$\text{Weight Percent Poly(p-dioxanone)} = (215.6212/\text{Mole Percent Polymerized Lactide})^{2.7027}$$

when the first absorbable polymer type does not comprise carboxylic acid capped oligomer and the poly(p-dioxanone) comprises carboxylic acid capped oligomer. The novel polymer blend provides dimensional stability to a manufactured article.

Yet another aspect of the present invention is an absorbable polymer blend. The blend has a first absorbable polymer type and a second absorbable polymer type. The first absorbable polymer type comprises at least 50 weight percent of the blend and further comprises about 100 mole percent to about 70 mole percent polymerized lactide and about 0 mole percent to about 30 mole percent polymerized glycolide; and, the second absorbable polymer type comprises poly(p-dioxanone). The maximum weight percent of poly(p-dioxanone) in the blend is 50 weight percent and the minimum weight percent of poly(p-dioxanone) in the blend is sufficient so that the polymer blend effectively provides dimensional stability to a manufactured article. The first absorbable polymer type or the second absorbable polymer type or the first absorbable polymer type and the second absorbable polymer type comprise a polymeric component and an oligomeric component. The polymeric component has a higher weight average molecular weight than the oligomer component and wherein at least one of said components is at least partially end-capped by a carboxylic acid. The minimum weight percent of poly(p-dioxanone) in the blend depends upon the molar amount of polymerized lactide in the first absorbable polymer type and is calculated by the expression:

$$\text{Weight Percent Poly(p-dioxanone)} = (215.6212/\text{Mole Percent Polymerized Lactide})^{2.7027} - 3.6273$$

when the first absorbable polymer type comprises carboxylic acid capped oligomer and the poly(p-dioxanone) either comprises or does not comprise carboxylic acid capped oligomer, and wherein the polymer blend provides dimensional stability to a manufactured article.

Still yet another aspect of the present invention is a medical device made from the above-described polymer blends.

A further aspect of the present invention is a method of manufacturing a medical device using the above-described polymer blends.

These and other aspects and advantages of the present invention will become more apparent from the following description and accompanying drawings.

DETAILED DESCRIPTION OF THE INVENTION

Figure 1:
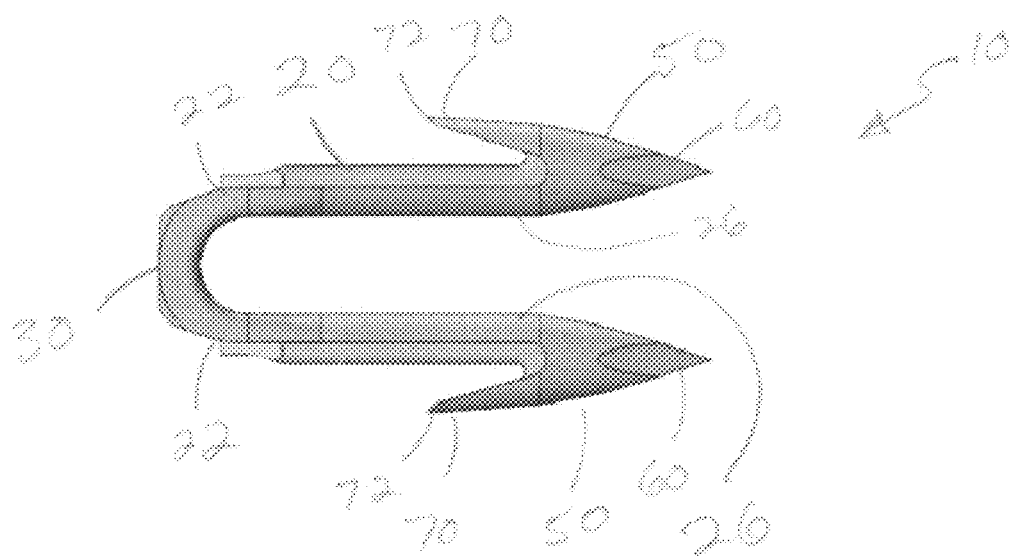
FIG. 1 is a drawing of an implantable staple or tack demonstrating the present invention, and shows a device with a small cross-sectional area.

Commonly-owned, co-pending U.S. patent application Ser. Nos. 12/887,995 and 13/833,690 are incorporated by reference herein in their entirety.

The novel polymer blends of the present invention are made from absorbable polyester polymers and copolymers. Preferably, one of the blend components is either poly(L(−)-lactide), or a lactide-rich lactide/glycolide copolymer. Another blend component is the absorbable polymer, poly(p-dioxanone).

The poly(L(−)-lactide), or a lactide-rich lactide/glycolide copolymer will be manufactured in a conventional manner. A preferred manufacturing method is as follows: the lactone monomers are charged along with an alcohol initiator, a suitable catalyst, and dye if desired, into a conventional stirred pot reactor capable of maintaining a controlled atmosphere at a controlled pressure. After purging to remove oxygen, under a nitrogen atmosphere the reactants are heated with agitation to conduct a ring-opening polymerization. After a suitable time the formed resin is discharged and sized appropriately. The resin particles are subjected to a devolatilization process and are subsequently stored under vacuum. The mole percent of polymerized lactide and polymerized glycolide in the lactide-rich polymer useful in the novel blends of the present invention may be varied to provide desired characteristics. Typically, the mole percent of polymerized lactide in the lactide-rich polymer will be about 70 percent to about 100 percent, more typically about 80 percent to about 90 percent, and preferably about 83 percent to about 87 percent. When the polymerized lactide in the lactide-rich polymer is 100 percent, the polymer is polylactide; poly(L(−)-lactide) is preferred for some surgical applications. Typically, the mole percent of polymerized glycolide in the lactide-rich polymer will be about 0 percent to about 30 percent, more typically about 10 percent to about 20 percent, and preferably about 13 percent to about 17 percent. In the case of carboxylic acid capped polymer, it would be necessary to cap the end group(s) with a carboxylic acid, conveniently accomplished by reaction with a cyclic anhydride.

The poly(L(−)-lactide) homopolymer, or a lactide-rich lactide/glycolide copolymer is characterized by chemical analysis. These characteristics include, but are not limited to, an inherent viscosity range from about 0.60 dL/g to about 2.25 dL/g, as measured in hexafluoroisopropanol at 25° C. and at a concentration of 0.1 g/dL. Gel permeation chromatography analysis showed a weight average molecular weight range from approximately 35,000 Daltons to 175,000 Daltons. It is to be understood that higher molecular weight resins can be employed provided the processing equipment used to form the blend, and to form the medical device, is capable of handling the melt viscosities inherent to these higher molecular weights and may be desirable for certain applications. For example, in some applications, a resin with an inherent viscosity of 2.5 dL/g may be needed to produce medical devices requiring certain characteristics, such as higher strength. Differential scanning calorimetry showed a glass transition temperature range from 20° C. to 65° C. and a melting transition from approximately 120° C. to 180° C. Nuclear magnetic resonance analysis confirmed that the copolymeric resin was a random copolymer of L(−)-lactide and glycolide. X-ray diffraction analysis showed a crystallinity level of approximately 20 to 45 percent.

It is to be understood that the polylactide homopolymer blend component, or a lactide-rich lactide/glycolide copolymer blend component, can be based on the lactide monomer of LL configuration, that is, L(−)-lactide. However, other stereo-chemical isomers can be substituted provided that in the final device, the lactide based polymer component exhibits sufficient crystallinity to effectively provide dimensional stability. Thus, the homopolymer, poly(D(+)-lactide) based on the DD configuration might be used instead of poly(L(−)-lactide). A lactide/glycolide copolymer component might be based entirely on the DD-isomer, or have mixtures of the DD-isomer and the LL-isomer, provided the crystallinity requirement in the final device is met. Meso-lactide, the DL-isomer might also be used in small proportions, again provided the crystallinity requirement in the final device is met.

The poly(p-dioxanone) polymer useful in the novel polymer blends of the present invention is manufactured in a conventional manner. A preferred method of manufacturing such polymer is as follows: the lactone monomer is charged along with an alcohol initiator, a suitable catalyst, and dye if desired, into a conventional stirred pot reactor. The dye should be one acceptable for clinical use; these include D&C Violet No. 2 and D&C Blue No. 6. After purging to remove oxygen, the reactants are heated under a nitrogen atmosphere with agitation to conduct a ring opening polymerization. After a suitable time, the formed resin is discharged into appropriate containers, and further polymerized under conditions known as "solid state" polymerization. An alternative method may include polymerization in the melt. After this reaction period is complete, the polymer resin is sized appropriately. The resin particles are subjected to a devolatilization process to remove unreacted monomer and are subsequently stored under vacuum. The poly(p-dioxanone) polymers useful in the blends of the present invention will have an inherent viscosity of at least about 0.80 dL/g as measured at 25° C. and at a concentration of 0.1 g/dL. The poly(p-dioxanone) polymers particularly useful in the blends of the present invention will have the following characteristics which include, but are not limited to: an inherent viscosity range from about 0.80 dL/g to about 2.30 dL/g, as measured in hexafluoroisopropanol at 25° C. and at a concentration of 0.1 g/dL. Gel permeation chromatography analysis showed a weight average molecular weight range from approximately 35,000 Daltons to 175,000 Daltons. It is to be understood that higher molecular weight resins can be employed, provided the processing equipment used to form the blend, and to form the medical device, is capable of handling the melt viscosities inherent to these higher molecular weights, and may be desirable for certain applications. For example, in some applications, a resin with an inherent viscosity of 2.5 dL/g may be needed to produce medical devices requiring certain characteristics, such as higher strength. Differential scanning calorimetry for this resin showed a glass transition temperature range from −15° C. to −8° C. and a melting transition from approximately 100° C. to 107° C. Nuclear magnetic resonance analysis confirmed that the resin was a homopolymer of poly(p-dioxanone), with a composition of approximately 98 percent polymerized p-dioxanone, and approximately 0 to 2 percent p-dioxanone monomer, as measured on a molar basis. X-ray diffraction analysis typically showed a crystallinity level of approximately 25 to 40 percent, although levels of 55 percent or higher have been observed. In the case of carboxylic acid capped poly(p-dioxanone), it would be necessary to cap the end group(s) with a carboxylic acid, conveniently accomplished by reaction with a cyclic anhydride.

The novel polymer blends of the present invention having improved dimensional stability will typically contain an absorbable polymer blend, comprising a first absorbable polymer type, the first absorbable polymer type comprising at least 50 weight percent of the blend and comprising about 100 mole percent to about 70 mole percent polymerized lactide and about 0 mole percent to about 30 mole percent polymerized glycolide; and, a second absorbable polymer type, the second polymer type comprising poly(p-dioxanone), wherein the maximum weight percent of poly(p-dioxanone) in the blend is 50 weight percent and the minimum weight percent of poly(p-dioxanone) in the blend is high enough so that the polymer blend provides dimensional stability to a manufactured article. Wherein further the first absorbable polymer type or the second absorbable polymer type or the first absorbable polymer type and the second absorbable polymer type comprise a first polymeric component and a second polymeric component, wherein the first polymeric component has a higher weight average molecular weight than the second polymeric component and wherein at least one of said components is at least partially end-capped by a carboxylic acid.

To be clear, the novel polymer blends of the present invention are typically a blend of a lactide-rich lactide/glycolide copolymer or a polylactide homopolymer, and poly(p-dioxanone). For example, the lactide/glycolide copolymer can be poly(L(−)-lactide-co-glycolide) having a composition of 85 mole percent polymerized lactide and 15 mole percent polymerized glycolide. The maximum weight percent of poly(p-dioxanone) in the blend is about 50. The minimum amount of poly(p-dioxanone) is the amount necessary to provide dimensional stability to a medical device. The blend of the present invention and the medical devices made therefrom will additionally comprise blend components that have been capped, preferably by reaction with a cyclic anhydride to result in carboxylic acid end groups. More preferably, the capped polymer components are lower molecular weight chains. These carboxylic acid capped oligomers allow the incorporation of a significant amount of carboxylic acid groups while still allow the overall blend to maintain a high weight average molecular weight.

Thus for the case of an 85/15 (mole basis) lactide/glycolide copolymer, the minimum weight percent poly(p-dioxanone) can be determined experimentally.

The blends of the present invention showed a crystallinity level of at least about 15 percent, typically greater than about 25 percent, and more preferably, greater than about 35 percent, as measured by x-ray diffraction.

The novel polymer blends of the present invention can be manufactured from the individual components in a variety of conventional manners using conventional processing equipment. Examples of manufacturing processes include chemical reactions of the ring-opening and polycondensation type, devolatilization and resin drying, dry blending in a tumble dryer, solution blending, extrusion melt-blending, injection molding, thermal annealing, and ethylene oxide sterilization processes. An alternate to dry blending with subsequent melt blending of the mixture can include the use of two or more feeders, preferably loss-in-weight feeders, that supply the components to be blended to an extruder; the extruder can be of the single screw or twin screw variety. Alternately, multiple extruders can be used to feed melts of the blend components, such as in co-extrusion.

The blends of the present invention may be made by thermal processes. Examples of thermal processes to produce the polymer blends of the present invention would be melt-blending in an extruder which can include twin screw blending or single screw extrusion, co-extrusion, twin screw blending with simultaneous vented-screw vacuum devolatilization, vacuum tumble drying with thermal devolatilization, monomer removal by solvent extraction at elevated temperature, and resin annealing.

In some cases it may be possible and desirable to use solution processing techniques, such as solution spinning, gel spinning and electro spinning. Other examples of conventional manufacturing process equipment that may be used to manufacture the novel polymer blends of the present invention may include single-screw and twin-screw compounders that operate on a continuous basis or batch-style compounders.

The polymer components, as well as blends of the subject invention can be sized by conventional means such as pelletization, granulation, and grinding.

A further embodiment of the present invention would be feeding appropriately sized particles of the blend components directly to the hopper of the injection molding machine. It would be apparent to one skilled in the art to apply this technique to other processing methodologies, such as, but not limited to, film or fiber extrusion. Limiting the thermal history of the polymer blend components is advantageous in that it avoids the possibility of premature degradation. Additional methods of thermal processing can include a process selected from the following group: injection molding, compression molding, blow molding, blown film, thermoforming, film extrusion, fiber extrusion, sheet extrusion, profile extrusion, melt blown nonwoven extrusion, co-extrusion, tube extrusion, foaming, rotomolding, calendaring, and extrusion. As noted earlier, appropriately sized particles of the blend components can be blended in the melt using these thermal processing means.

Although not wishing to be held to scientific theory, it is believed that the morphological development in the final part is greatly influenced by the device forming process, such as injection molding. Thus the melt blended resin may have a morphology with a very low aspect ratio for the minor phase, poly(p-dioxanone). It may not be until the high shear device forming process (e.g., injection molding), that the high aspect ratio of the minor phase is realized.

Other examples of manufacturing process equipment include chemical reactors ranging in size from two-gallon to seventy-five gallon capacity, process devolatilization dryers ranging from one cubic feet to twenty cubic feet, single and twin-screw extruders from about one inch to about three inches in diameter, and injection molders ranging from about seven to about 40 tons in size.

If desired, the polymer blends of the present invention may contain other conventional components and agents. The other components, additives or agents will be present to provide additional effects to the polymer blends and medical devices of the present invention including antimicrobial characteristics, controlled drug elution, radio-opacification, and osseointegration.

Such other components will be present in a sufficient amount to effectively provide for the desired effects or characteristics. Typically, the amount of the other adjuncts will be about 0.1 weight percent to about 20 weight percent, more typically about 1 weight percent to about 10 weight percent and preferably about 2 weight percent to about 5 weight percent.

Examples of antimicrobial agents include the polychloro phenoxy phenols such as 5-chloro-2-(2,4-dichlorophenoxy) phenol (also known as Triclosan).

Examples of radio-opacification agents include barium sulfate while examples of osseointegration agents include tricalcium phosphate.

The variety of therapeutic agents that can be used in the polymer blends of the present invention is vast. In general, therapeutic agents which may be administered via pharmaceutical compositions of the invention include, without limitation, antiinfectives, such as antibiotics and antiviral agents; analgesics and analgesic combinations; anorexics; antihelmintics; antiarthritics; antiasthmatic agents; adhesion preventatives; anticonvulsants; antidepressants; antidiuretic agents; antidiarrheals; antihistamines; anti-inflammatory agents; antimigraine preparations; contraceptives; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; cough and cold preparations, including decongestants; hormones, such as estradiol and other steroids, including corticosteroids; hypnotics; immunosuppressives; muscle relaxants; parasympatholytics; psychostimulants; sedatives; tranquilizers; naturally derived or genetically engineered proteins, polysaccharides, glycoproteins, or lipoproteins; oligonucleotides, antibodies, antigens, cholinergics, chemotherapeutics, hemostatics, clot dissolving agents, radioactive agents and cystostatics. Therapeutically effective dosages may be determined by in vitro or in vivo methods. For each particular additive, individual determinations may be made to determine the optimal dosage required. The determination of effective dosage levels to achieve the desired result will be within the realm of one skilled in the art. The release rate of the additives may also be varied within the realm of one skilled in the art to determine an advantageous profile, depending on the therapeutic conditions to be treated.

Suitable glasses or ceramics include, but are not limited to phosphates such as hydroxyapatite, substituted apatites, tetracalcium phosphate, alpha- and beta-tricalcium phosphate, octacalcium phosphate, brushite, monetite, metaphosphates, pyrophosphates, phosphate glasses, carbonates, sulfates and oxides of calcium and magnesium, and combinations thereof.

Suitable polymers that may be included in the polymer blends of the present invention include: suitable biocompatible, biodegradable polymers which may be synthetic or natural polymers. Suitable synthetic biocompatible, biodegradable polymers include polymers selected from the group consisting of aliphatic polyesters, poly(amino acids), copoly (ether-esters), polyalkylenes oxalates, polyamides, tyrosine derived polycarbonates, poly (iminocarbonates), polyorthoesters, polyoxaesters, polyamidoesters, polyoxaesters containing amine groups, poly (anhydrides), polyphosphazenes, polydiglycolates, and combinations thereof. It is to be understood that inclusion of additional suitable polymers is dependent upon obtaining dimensional stability in the fabricated device.

For the purposes of this invention the above-mentioned optional aliphatic polyesters include, but are not limited to, homopolymers and copolymers of lactide (which include lactic acid, D-, L- and meso lactide), glycolide (including glycolic acid), epsilon-caprolactone, p-dioxanone (1,4-dioxan-2-one), trimethylene carbonate (1,3-dioxan-2-one), alkyl derivatives of trimethylene carbonate, and blends thereof.

Suitable natural polymers include, but are not limited to, collagen, elastin, hyaluronic acid, laminin, gelatin, keratin, chondroitin sulfate and decellularized tissue.

Although not preferred, the medical devices of the present invention may contain nonabsorbable polymers in addition to the absorbable polymer blends of the present invention. Examples of such devices may include but are not limited to meshes, sutures, and staples, where the properties of both the absorbable and nonabsorbable polymers are advantageous.

Suitable nonabsorbable polymers include, but are not limited to, acrylics; polyamide-imide (PAI); polyaryletherketones (PEEK); polycarbonates; thermoplastic polyolefins such as polyethylene (PE), polypropylene (PP), polymethylpentene (PMP), and polybutene-1 (PB-1); polyolefin elastomers (POE) such as polyisobutylene (PIB), ethylene propylene rubber (EPR); polybutylene terephthalate (PBT); polyethylene terephthalates (PET); polyamides (PA) such as nylon 6 and nylon 66; polyvinylidene fluoride (PVDF); polyvinylidene fluoride-co-hexafluropropylene (PVDF/HFP); polymethylmethacrylate (PMMA) and combinations thereof and equivalents.

The novel absorbable medical devices of the present invention that are made from the novel absorbable polymer blends of the present invention include, but are not limited to, conventional medical devices, especially fibrous devices such as monofilament-based and multifilament-based sutures and meshes, woven fabrics, nonwoven fabrics, knitted fabrics, fibrous bundles, cords, and other implantable medical devices, including staples, tacks, clips, tissue fixation devices, mesh fixation devices, anastomotic devices, suture anchors and bone anchors, tissue and bone screws, bone plates, prostheses, support structures, tissue augmentation devices, tissue ligating devices, patches, substrates, tissue engineering scaffolds, composites, bone grafts, drug delivery devices, stents, bone waxes and bone fillers, combinations and equivalents.

An example of a medical device that can be molded from the polymer blends of the present invention is a tissue tack 10 as seen in FIG. 1. FIG. 1 is a drawing of an implantable staple or tack demonstrating the present invention, and shows a device with a small cross-sectional area. The material of this device must be inherently stiff if the tack is to function properly for the intended application.

Figure 2:
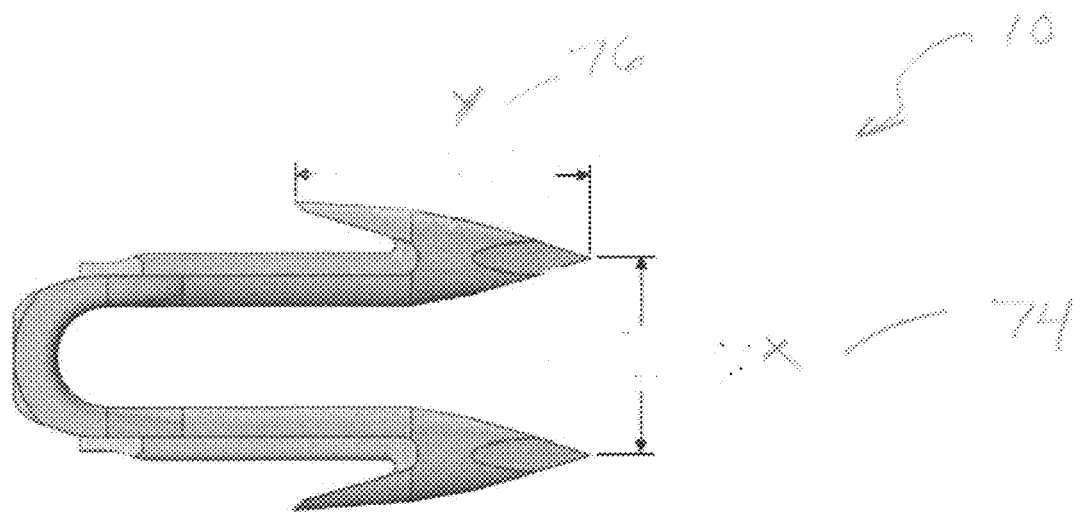
FIG. 2 is a drawing of the device of FIG. 1 showing critical dimensions of said device.
Figure 3:
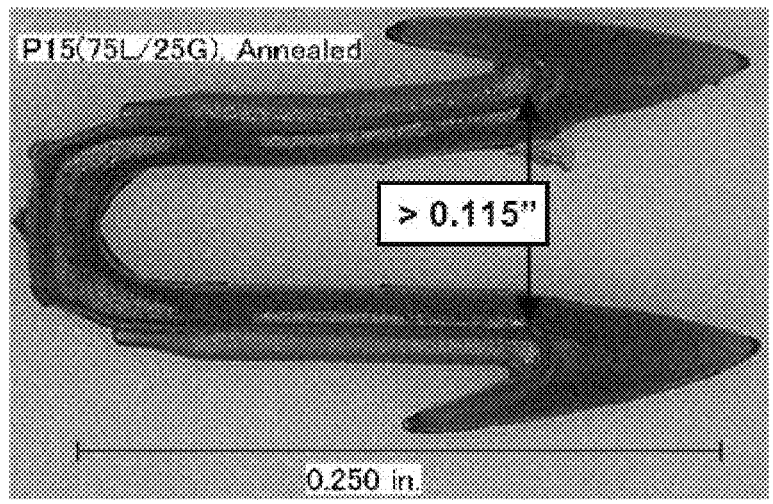
FIG. 3 is a photograph of an injection molded tack of the device of FIG. 1 exhibiting poor dimensional stability and an unacceptable level of warping after thermal annealing.
Figure 4:
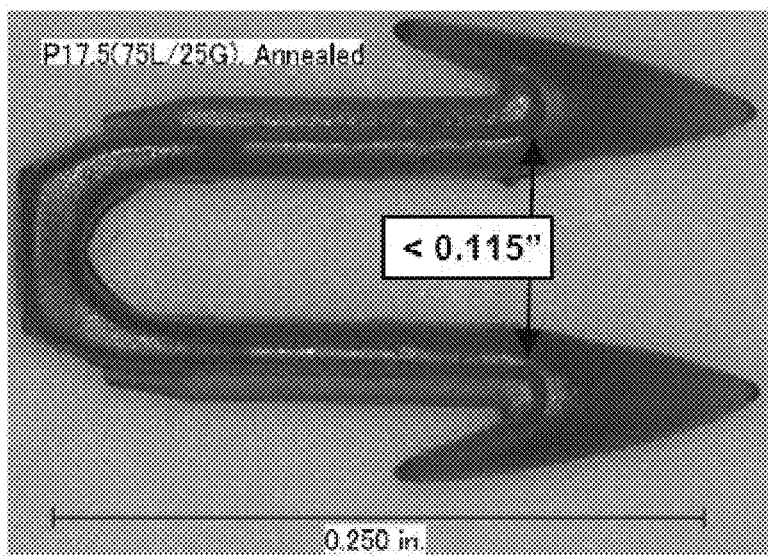
FIG. 4 is a photograph of an injection molded tack of the device of FIG. 1 exhibiting superior dimensional stability and an acceptable level of warping after thermal annealing.

The tack 10 is seen to have two leg members 20 connected by a connecting strap member 30 at their proximal ends 22. The distal ends 26 are seen to have barb members 50 extending distally therefrom. Barb members 50 have distal tissue piercing points 60 and proximal barbs 70 having points 72. Referring to FIG. 2, barb members 50 are seen to have a length 74 shown as dimension Y. The points 60 are seen to be spaced apart by a distance 76 shown as dimension X.

Suitable tacks that can be made from the polymer blends of the present invention are also disclosed and described in commonly-assigned U.S. patent application Ser. Nos. 12/464,143; 12/464,151; 12/464,165; and, 12/464,177, which are incorporated by reference.

The ability of the injection molded articles to develop some level of crystallinity prior to annealing allows the parts to undergo an annealing cycle to further crystallize the poly(lactide-co-glycolide) phase of the blend without unduly warping or shrinking, that is while maintaining dimensional integrity.

Injection molded parts of the blends of the subject invention can advantageously be subjected to an annealing cycle to mature the polymer morphology. This often increases the level of crystallinity in the part. This process helps to ensure that when the part is exposed to moderately elevated temperatures, especially when exposed to ethylene oxide during sterilization, dimensional stability will be acceptable. Although not wanting to be held to scientific theory, it is believed that directly after injection molding, under many processing conditions, the articles are almost completely amorphous, but when stored at room temperature the poly (p-dioxanone) phase in the blend begins to crystallize. Polymeric materials will only crystallize when stored at temperatures above their glass transition temperature. The glass transition temperature of poly(p-dioxanone) is about minus 10° C., allowing the poly(p-dioxanone) to begin crystallizing during storage at room temperature. In some processing conditions, typically at longer holding times in the mold, the poly(p-dioxanone) component can crystallize. The ejected parts then possess a small amount of crystallinity due substantially to this phase.

The ability of the poly(p-dioxanone) phase in the blend to develop some level of crystallinity prior to annealing allows for the crystallization of the poly(lactide-co-glycolide) phase without excessive distortion of the molded article. This is because the formation of an organized, semicrystalline, molecular structure increases the part's resistance to distortion at elevated temperatures. For instance, if an amorphous, 100% poly(lactide-co-glycolide) article were to be annealed, the part would likely warp during the annealing process if there were even moderate stress levels present. The interdispersed, semicrystalline poly(p-dioxanone) in the blend maintains the dimensional stability of the part during exposure to the elevated temperatures needed to crystallize the poly(lactide-co-glycolide) phase of the blend. The end result is a semicrystalline, dimensionally stable, injection molded article.

It is expected that if carboxylic acid end capped oligomers (low molecular weight polymer) are included in the overall blend, faster crystallization can take place with possible higher overall crystallinity levels being achieved in the medical devices formed thereof. This will increase the dimensional stability of the medical devices as compared to the medical devices made at the same overall composition but without the capped oligomer components. A net effect is the possibility of lowering the amount of poly(p-dioxanone) needed, advantageously resulting in an even stiffer device.

The medical devices of the present invention can be thermally annealed at a temperature of at least 45 degrees centigrade for at least one minute. More preferably, the medical devices of the present invention are thermally annealed at a temperature of about 60 degrees centigrade for about 8 hours, followed by annealing at a temperature of about 70 degrees centigrade for about 4 hours, followed by annealing at a temperature of about 80 degrees centigrade for about 4 hours.

The medical device of the present invention will exhibit a crystallinity level of at least about 15 percent, typically greater than about 25 percent, and more preferably, greater than about 35 percent, as measured by X-ray diffraction.

To further inhibit warping during the annealing process, the article may also be constrained mechanically by the use of an annealing fixture. Theoretically, it is possible to anneal the part fully confined, or constrained. This would require the equivalent of annealing in the mold. This, of course, is often economically not feasible. However, constraining a limited number of dimensions during annealing may be economically possible. Articles of the present invention can be annealed using an annealing fixture that supports the parts from distortion within the horizontal plane of the part. Although this annealing fixture is intended to aid in the resistance of distortion at elevated temperatures during annealing, it will not prevent dimensionally unstable parts from warping.

As the lactide level in the poly(lactide-co-glycolide) portion of the blend decreases, crystallization of the poly (lactide-co-glycolide) phase becomes more difficult. In blends using a poly(lactide-co-glycolide) copolymer less rich in polymerized lactide, an increased weight percent of poly(p-dioxanone) may be required to maintain dimensional stability of the molded article. Such copolymers include 70/30 poly(lactide-co-glycolide).

As noted earlier, the greater the amount of molecular orientation, or stress, present in the formed medical device, the greater will be the driving force to shrink or warp; shrinking and warping is usually viewed as a disadvantageous phenomenon.

In the formation of devices using processing means that induce at least a moderate level of molecular orientation, or stress, it would be an advantage to maintain dimensional stability. One such fabrication methodology that usually induces at least a moderate level of stress is injection molding. To be clear, when forcing a molten polymer stream through a pathway that is narrow, and finally into a cavity, one usually encounters high shear rates and high stress levels. When this happens, the molecular chains tend to orient in the direction of the flow, thereby setting up the system for later shrinkage or warpage when subjected to temperatures slightly elevated above the glass transition temperature, particularly during exposure to EO gas while sterilizing.

Evidence of a high shear forming process is the presence of high residual stresses in the part; these can be measured in a variety of ways. One such way is by viewing a part through crossed-polarized films. Other ways of assessing residual stresses utilize Scanning Electron Microscopy (SEM) techniques. The phase architecture of the substantially immiscible polymer blends of lactide/glycolide copolymers and poly(p-dioxanone) further provide evidence of the level of stress that the blend was subjected to during processing. When in high shear situations, usually the minor phase is non-spherical in nature. The minor phase usually distorts to elongated ellipsoids with L/Ds greater than about 3 to worm-like structures having L/D values 50 or greater. The medical devices of the present invention will typically have aspect ratios of the minor phase greater than about 3, more typically greater than about 5, and preferably greater than about 20. Depending on the shear field, one could envision non-circular cross-sections that are more ribbon-like. When the minor phase is substantially spherical in nature, one can conclude that: (1) the level of shear the polymer melt was subjected to was quite low or (2) the processing conditions employed allowed the polymer melt to relax, and the subsequent elongated domains reshaped to much lower L/D structures. In either case, the level of residual stress is expected to be low. A "sphere-only" minor phase morphology may then be evidence of low residual stress.

Conventionally known methods to ascertain phase architecture in immiscible polymer blends include phase contrast microscopy (polarized light microscopy); atomic force microscopy (AFM); electron microscopy including scanning, tunneling and transmission electron microscopy (SEM, STM, and TEM). Other techniques potentially include high resolution digital-optical microscopy.

Sample preparation may be via cryogenic fracturing or by microtoming techniques including cryogenic microtoming. Solvent etching has proven to be a useful sample preparation methodology in a number of systems.

As would be known to one having ordinary skill in the art, in accessing the morphology of the minor phase, it is important to realize that it is necessary to make measurements on the sample from different angular perspectives. Specifically, in parts having elongated features as might be found in the present article of this invention, an examination looking at only the cross-section may incorrectly indicate that the minor phase is spherical in nature. Only when assessed longitudinally will it be revealed that the minor phase is actually elongated in nature with a high aspect ratio.

The medical devices of the present invention will have an inherent viscosity of at least about 0.6 dL/g as measured in hexafluoroisopropanol at 25 degrees centigrade at a concentration of 0.1 g/dL. Additionally, the inherent viscosity of the lactide-rich polymer will be at least about 0.6 dL/g and the inherent viscosity of the poly(p-dioxanone) will be at least about 0.6 dL/g, both as measured in hexafluoroisopropanol at 25 degrees centigrade at a concentration of 0.1 g/dL.

The medical devices of the present invention will remain dimensionally stable when subjected to immersion in water at an elevated temperature. Preferably they will remain dimensionally stable when subjected to immersion in water at 49 degrees centigrade. Most preferably, they will remain dimensionally stable when subjected to immersion in water at 70 degrees centigrade. The water used in these tests of dimensional stability is present as a heat transfer medium and thus may be pure water.

It should be clear to one having ordinary skill in the art that acid level might be expressed by a variety of methods. These include milliequivalents per gram (meq/gram). We intend to define the concept of an acid level to be used herein. One determines the number of moles of carboxylic acid groups attached to the chains of the resin under consideration. If the resin is a polylactone, one determines the number of moles of lactone monomer incorporated into said resin. The acid level is herein defined as the number of moles of said carboxylic acid groups attached to the chains, divided by the number of moles of said lactone monomer incorporated into said resin. In the case of resins containing polymeric repeat units not formed from lactones, the number of moles of repeat units will be included.

Thus if a resin was formed containing 10 moles of polymerized glycolide and 90 moles of polymerized lactide, and had end groups corresponding to 1.7 moles of carboxylic acid groups, one could calculate that the resin had an acid level of 1.7 percent [100×1.7/(90+10)=1.7]. In another example, if a resin was formed containing 81 moles of polymerized lactide, 9 moles of polymerized glycolide, and 10 moles of repeat units of hexamethylene adipate, and had end groups corresponding to 2.0 moles of carboxylic acid groups, one could calculate that this second resin had an acid level of 2.0 percent [100×2.0/(81+9+10)=2.0].

For a medical device of the present invention, such as a surgical suture or a molded fixation device, based on a polylactide or a lactide-rich copolymer, the minimum acid level is 0.3 percent and the maximum acid level that can be incorporated and still allow high mechanical properties is dependent on the molecular weight of the lower molecular weight blend component. When the lower molecular weight component is blended with a higher molecular weight blend component possessing a weight average molecular weight of 80,000 Daltons, the maximum acid level limit is approximately 12 percent when the initiator ratio for the lower molecular weight blend component value, $IR_2$, is 10; when $IR_2$ is 20, the maximum acid level limit is approximately 6 percent.

We have determined that when the lower molecular weight blend component is blended with a higher molecular weight blend component possessing a weight average molecular weight of 80,000 Daltons, the maximum acid level limit as a function of the initiator ratio for the lower molecular weight blend component value, $IR_2$, can be calculated by the following expression:

$$\text{Max acid level} = 110 \times IR_2^{-0.983} \tag{1}$$

We have determined that when the lower molecular weight component is blended with a higher molecular weight blend component possessing a weight average molecular weight of 120,000 Daltons, the maximum acid level limit as a function of the initiator ratio for the lower molecular weight blend component value, $IR_2$, can be calculated by the following expression:

$$\text{Max acid level} = 140 \times IR_2^{-0.994} \quad (2)$$

The initiator ratio, IR, is defined as the ratio of moles of monomers divided by the moles of initiator. $IR_1$ refers to the initiator ratio of the first blend component and $IR_2$ refers to the initiator ratio of the second blend component.

In some embodiments of the present invention, $IR_1$ values can range from about 250 to about 1200 and $IR_2$ values can range from about 8 to about 100.

Thus the maximum amount of acid that can be incorporated into the novel blends of the present invention is dependent on the $IR_2$ value, as well as the molecular weight of the higher molecular weight blend component. So when the value of $IR_2$ is 10, the maximum acid value is about 12 percent when the weight average molecular weight of the high molecular weight component is 80,000 Daltons, is about 14 percent when the weight average molecular weight of the high molecular weight component is 120,000 Daltons. Correspondingly, when the value of $IR_2$ is 20, the maximum acid value is about 6 percent when the weight average molecular weight of the high molecular weight component is 80,000 Daltons, and is about 7 percent when the weight average molecular weight of the high molecular weight component is 120,000 Daltons.

With lower values of $IR_2$, higher a maximum acid levels are possible. For instance, maximum acid levels of about 20 percent when the first polymeric component has a weight average molecular weight of 80,000 Daltons, and wherein the maximum acid level is about 26.5% when the first polymeric component has a weight average molecular weight of 120,000 Daltons.

The novel polymer blends of the present invention are made from absorbable polyester (co)polymers and (co)oligomers. Preferably, one of the blend components is a lactide/glycolide co-polymer. Another blend component may be a lactide/glycolide co-oligomer with a substantial number of end groups acidic in nature. Yet another possible blend component may be poly(p-dioxanone) with a substantial number of end groups acidic in nature.

The blends of the present invention have a number of embodiments. Three preferred embodiments will now be described as Categories or Cases I, II and III.

Case I refers to situations in which the first absorbable polymer type is made up of a mixture of an L/G copolymer and an L/G oligomer capped with carboxylic acid groups. Other embodiments of the present invention include situations in which the first absorbable polymer type is made up of a mixture of a polylactide homopolymer and a homooligomer capped with carboxylic acid groups.

Case II refers to situations in which the second absorbable polymer type is made up of a mixture of a poly(p-dioxanone) and a p-dioxanone oligomer capped with carboxylic acid groups.

Case III refers to situations in which the first absorbable polymer type is made up of a mixture of a L/G copolymer and a L/G oligomer capped with carboxylic acid groups, and the second absorbable polymer type is made up of a mixture of a poly(p-dioxanone) and a p-dioxanone oligomer capped with carboxylic acid groups. Again, other embodiments of the present invention include situations in which the first absorbable polymer type is made up of a mixture of a polylactide homopolymer and a homooligomer capped with carboxylic acid groups.

The lactide/glycolide copolymer will be manufactured in a conventional manner. A preferred manufacturing method is as follows. Lactone monomers are charged along with an alcohol initiator, a suitable catalyst, and dye if desired, into a conventional stirred pot reactor. After purging to remove oxygen, under a nitrogen atmosphere, the reactants are heated with agitation to conduct a ring-opening polymerization. After a suitable time the formed resin is discharged and sized appropriately. The resin particles are subjected to a devolatilization process and are subsequently stored under vacuum. The mole percent of polymerized lactide and polymerized glycolide in the lactide-rich co-polymer useful in the novel blends of the present invention may be varied to provide desired characteristics. Typically, the mole percent of polymerized lactide in the lactide-rich polymer will be about 70 percent to about 100 percent, and more typically about 85 percent to about 95 percent. When the polymerized lactide in the lactide-rich polymer is 100 percent, the polymer is polylactide; polylactide is preferred for some surgical applications. Typically, the mole percent of polymerized glycolide in the lactide-rich co-polymer will be about 0 percent to about 30 percent, and more typically about 5 percent to about 15 percent.

It was found that the polymers of the present invention can be made utilizing conventional metal-based catalysts such as tin catalysts or titanium catalysts. Tin catalysts include stannous octoate and stannous chloride. We have additionally found that the level of catalyst is advantageously in the range of about 3 to 30 ppm, based on the metal content.

The respective amounts of the higher and lower molecular weight polymeric components present in the novel blends of the present invention will be sufficiently effective to provide the desired characteristics and properties. The novel absorbable polymeric blends of the present invention will typically contain about 1.25 wt. % to about 50 wt. % of the lower molecular weight component, more typically about 12 wt. % to about 22 wt. %. The higher molecular weight component will typically make up the remainder of the blends.

Table 1 describes parameters and ranges for the novel polymer blends of the present invention. As mentioned earlier, there are a variety of embodiments in which the polylactide or lactide-rich lactide/glycolide copolymer is carboxylic acid capped, or the poly(p-dioxanone) is carboxylic acid capped, or both are carboxylic acid capped. For a given polymer that is capped, $IV_1$ refers to the inherent viscosity of higher molecular weight blend component 1, $IV_2$ refers to the inherent viscosity of corresponding lower molecular weight blend component 2, $IV_{BLEND}$ refers to the inherent viscosity of the blend. Similarly, $M_{w1}$ refers to the weight-average molecular weight of blend component 1, $M_{w2}$ refers to the weight-average molecular weight of blend component 2, $M_{wBLEND}$ refers to the weight-average molecular weight of the blend and $M_{wDEVICE}$ refers to the weight-average molecular weight of the device. Inherent viscosity measurements were made at a concentration of approximately 0.1 g/dL at 25° C. in hexafluoroisopropanol (HFIP).

TABLE 1

| Factor | Dimensions | Minimum Value | Preferred Operating Range | Max Value |
|---|---|---|---|---|
| $IV_1$ | dL/g | 0.9 | 1.4 to 1.7 Preferred: 1.45 to 1.55 | 2.5 |
| $IV_2$ | | 0.1 | 0.20 to 0.25 Preferred: 0.22 to 0.23 | 0.65 |
| $IV_{BLEND}$ | | 0.8 | 1.1 to 1.4 Most Often Observed: 1.15-1.25 | 2 |
| $IV_{DEVICE}$ | | 0.5 | 0.90 to 1.05 Most Often Observed: 0.95 to 1.0 | 1.8 |
| $M_{w1}$ | Daltons | 42,000 | 75,000 to 100,000 Most Often Selected: 80,000 to 90,000 | 175,000 |
| $M_{w2}$ | | 1,400 | 4,700 to 5,200 Most Often Selected: 4,800 to 5,000 | 24,000 |
| $M_{wBLEND}$ | | 35,000 | 55,000 to 75,000 Most Often Observed: 58,000 to 65,000 | 120,000 |
| $M_{wDEVICE}$ | | 18,000 | 40,000 to 55,000 Most Often Observed: 42,000 to 46,000 | 100,000 |
| Acid Levels | Percent | 0.3 | 1.2 to 2.2 Most Often 1.7 | 23, when blended with a resin with an $M_w$ of 80 k Daltons[1] 28, when blended with a resin with an $M_w$ of 120 k Daltons[1] |
| Weight Percent of Low MW Component | Percent | 1.25 (assuming an $IR_2$ of 5) | 12 to 22 (using an $IR_2$ of 20) | Approximately 50 weight percent[1] |

(1) Maximum acid levels depend on the particular application (suture, etc.), the $M_w$ of the high molecular weight component, and on the value of $IR_2$
(2) Although $IV_{DEVICE}$ and $M_{wDEVICE}$ are listed in Table 1, these designators would apply to any medical device made from the inventive polymeric blends, not just fibers In some instances, articles can be made directly from the blend components by thermal processes; examples of this include direct melt extrusion of a physical mixture of the blend components or direct injection molding of a physical mixture of the blend components. To be clear, a physical mixture of the blend components is introduced to the supply hopper of the forming equipment, extruder, injection molder, etc. Because at least one of the components [the polylactide or lactide-rich lactide/glycolide copolymer blend component, or the poly(p-dioxanone) blend component] is a blend of a high molecular weight component and a low molecular weight component, the inventive blends of the present invention will have at least three components, one of which must be substantially carboxylic acid end capped. If both the polylactide or lactide-rich lactide/glycolide copolymer, and the poly(p-dioxanone) are blends of a high molecular weight component and a low molecular weight component, the inventive blends of the present invention will have at least four components, one of which must be substantially carboxylic acid end capped.

Nuclear magnetic resonance analysis can be used to confirm that the dried co-polymeric resin is a random copolymer of glycolide and lactide. It is to be understood that different isomers of lactide can be used, such as L(−)-lactide or D(+)-lactide or meso-lactide.

The characteristics of the polymer blends of the present invention will be sufficiently effective to provide the needed physical properties to allow the surgical devices to function as intended, yet lose these mechanical properties at a rate much quicker than convention synthetic absorbable polymers of like composition.

For the purpose of this application we wish to define the term of capping or end-capping. Capping or end-capping is the chemical modification of the polymer chain termini. These terms also refer to the chemical modification of the chain termini of low molecular weight polymers or oligomers. For clarification purposes, consider ring-opening polymerization where one starts with an initiator and lactone monomers. First consider a monofunctional alcohol initiator such as 1-dodecanol. In this case the resulting polymer chains have alkyl functionality on one end and an alcoholic functionality on the other. One can now chemically modify the alcoholic functionality into a carboxylic functionality. This can be conveniently accomplished by reaction of the alcohol chain end with a cyclic anhydride, such as diglycolic anhydride or succinic anhydride. For the purposes of this application we can describe this polymer to be end-capped with carboxylic acid functionality.

Similarly, one could consider using an initiator containing both carboxylic acid functionality and an alcohol group, such as glycolic acid. In this case the resulting polymer chains have carboxylic acid functionality on one end and an alcoholic functionality on the other. One can now again chemically modify the alcoholic functionality into carboxylic acid functionality. For the purposes of this application we can describe this polymer to be end-capped with carboxylic acid functionality. To be clear, we do not consider the glycolic acid initiated polymer to be end-capped until its end is converted into a carboxylic acid, for example by further reaction with a cyclic anhydride.

Finally, one could consider using an initiator containing two alcohol functionalities, such as diethylene glycol. In this case the resulting polymer chains have alcoholic functionalities on both ends. One can now chemically modify both alcoholic functionalities into carboxylic acid functionalities, for instance by reaction of the formed polymer/oligomer with a cyclic anhydride. For the purposes of this application we can describe the latter two polymers to be end-capped with carboxylic acid functionality.

It should be clear to those having ordinary skill in the art that the capping can be achieved in multiple ways. These ways could also include, for example, direct oxidation of the chain ends.

In one embodiment of the present invention the polymer blend contains a conventional dye. The dye should be one acceptable for clinical use; this includes, without limitation, D&C Violet No. 2 and D&C Blue No. 6 and similar combinations thereof. It should be noted that one or more of the blend components may be dyed or the dye can be introduced during the blend compounding stage. Additionally, in another embodiment, one polymeric component of the blend might be colored with a first dye at a given concentration, and the second polymeric component colored with the same or another dye at the same or another concentration.

Such other components (dyes, etc.) will be present in a sufficient amount to effectively provide for the desired effects or characteristics. Typically, the amount of the other adjuncts (other components) will be about 0.01 weight percent to about 20 weight percent, more typically about 0.1 weight percent to about 10 weight percent and preferably about 0.1 weight percent to about 5 weight percent based on the total weight of the blend. In the special case of colorants, preferred amounts typically range from about 0.02 to about 0.2 weight percent of the final device.

For purposes of this application, we wish to use the term suture to mean surgical sutures, and more broadly fibrous devices, including monofilament and multifilament yarns used in the medical field. These include, but are not limited to, fibers used to make surgical meshes; and, fibers used to make surgical fabrics and tapes made by any known method of processing (knitted, woven, nonwoven, etc.). The sutures of the present invention may be used for a variety of applications including, but not limited to wound fixation, wound closure, general tissue approximation, and attachment of implants.

Modern surgical sutures generally range from Size 5 (heavy braided suture for orthopedics) to Size 11/0 (for example, a fine monofilament suture for ophthalmics). The actual diameter of thread for a given U.S.P. size differs depending on the suture material class. The diameters of sutures in the synthetic absorbable suture class are listed in the United States Pharmacopeia (USP) as well as in the European Pharmacopoeia. The USP standard is more commonly used.

The polymeric components of the medical devices of the present invention will have an inherent viscosity of at least about 0.5 dL/g as measured in hexafluoroisopropanol at 25° C. at a concentration of 0.1 g/dL, provided the medical device is fully soluble in this solvent.

Injection Molding

Injection molding is a process well-known in the plastic industry. It is designed to produce parts of various shapes and sizes by melting the plastic, mixing and then injecting the molten resin into a suitably shaped mold. After the resin is solidified, the part is generally ejected from the mold and the process continued.

For the purposes of this invention, a conventional 30-ton electrically controlled injection molding machine can be used. The polymer blends of the present invention can be processed in the following general manner. The polymer and polymer blends can be fed by gravity from a hopper, under nitrogen purge, into a heated barrel. The polymer will generally move forward in the barrel by the screw-type plunger into a heated chamber. As the screw is advanced forward, the molten polymer and polymer blends will be forced through a nozzle that rests against a mold, allowing the polymer and polymer blends to enter a specially designed mold cavity, through a gate and runner system. The blend will be formed into the part in the mold cavity, and then allowed to cool at a given temperature for a period of time. It will be then removed from the mold, or ejected, and separated from the gate and runner.

A further aspect of the novel polymer blends of the present invention is the persistence of weight-average molecular weight upon thermal processing. A benefit of having the weight-average molecular weight not change much during thermal processing, such as melt extrusion, is the enabling of higher mechanical properties in the fabricated devices so produced. We have found that in the case of producing multifilament yarns, a minimum weight-average molecular weight of about 35,000 Daltons in the yarns is desirable. If the weight-average molecular weight of the polymer blend drops too much during thermal processing, it would be difficult to achieve a minimum weight-average molecular weight in the resulting medical device, and hence, not allowing the part to possess the minimum desired mechanical properties.

An additional further aspect of the novel absorbable polymer blends of the present invention is the incorporation of an additional polymeric component, wherein said additional polymeric component is selected from the group consisting of non-absorbable polymers, rapidly absorbing polymers, and slowly absorbing polymers.

Problem to Be Solved I

Consider blends of a poly(lactide-co-glycolide) (L/G) copolymer and poly(p-dioxanone) (PDS), at a given weight percent of PDS, for example an 85/15 L/G copolymer blended with 20 weight percent of PDS. If one wanted to improve certain mechanical properties of the blend, e.g., provide a material that is stiffer, one could increase the mole percent of polymerized lactide in the lactide/glycolide copolymer. Consider for example a 95/5 L/G copolymer; this change would increase the overall crystallinity level in the blend and make the blend mechanically stiffer. It should also be noted that this scenario also raises the glass transition temperature of the lactide/glycolide copolymer, helping to further achieve higher stiffness. There is however an unintended problem when increasing the mole percent lactide in the lactide/glycolide copolymer: the blend takes longer to absorb post-implantation.

Solution to Problem I

It was found that by blending either the first absorbable polymer type, or the second absorbable polymer type or the first and the second absorbable polymer type with a lower molecular weight component, wherein at least one of the two components is at least partially end-capped by a carboxylic acid we have been able to provide a polymer blend of high modulus suitable for making dimensionally stable implantable medical devices that absorb in a shorter time frame than previously available absorbable blends. To be clear, for a given lactide/glycolide copolymer composition, and a given weight percent of poly(p-dioxanone), the blends of the present invention absorb faster thus lowering the time to absorb post-implantation.

Problem to Be Solved II

Consider blends of a poly(lactide-co-glycolide) copolymer and poly(p-dioxanone) [PDS], at a given lactide/glycolide ratio. Say, 90/10 L/G copolymer blended with 11 weight percent PDS. If one wanted the material to be stiffer, one could attempt to decrease the poly(p-dioxanone) making the blend behave mechanically stiffer. One may then risk lowering the dimensional stability of the molded parts produced therefrom.

There is then the unintended problem when decreasing the poly(p-dioxanone) weight percent level too much, that the blend no longer results in dimensionally stable parts.

Solution to Problem II

It was found that by blending either the first absorbable polymer type, or the second absorbable polymer type or the first and the second absorbable polymer types with a lower molecular weight component, wherein at least one of the two components is at least partially end-capped by a carboxylic acid, we have been able to provide a polymer blend suitable for making implantable medical devices that still possesses good dimensional stability in molded parts that have higher moduli than previously available absorbable blends by virtue of having a lower poly(p-dioxanone) weight percent. Dimensional stability of these present inventive blends was also enhanced. For example, using a 95/5 poly(lactide-co-glycolide) copolymer, the minimum amount of poly(p-dioxanone) required to produce dimensionally stable parts is 9.2 weight percent of the blend. Using the inventive concepts described herein, one could reduce the reduce the weight percent of poly(p-dioxanone) in the blend, to say 5.5 weight percent and still be able to achieve dimensionally stable medical devices made therefrom; these parts however would have a higher stiffness than parts made from a blend based on 9.2 weight percent of poly(p-dioxanone) and 90.8 weight percent of a 95/5 L/G copolymer. An additional benefit of the present invention is a decrease in the time needed to absorb the medical part in the body.

Further Details

The novel polymer blends of the present invention are made from a combination of absorbable polyester polymers and copolymers that are at least partially end-capped by a carboxylic acid group. Preferably, the first absorbable polymer type is either poly(L(−)-lactide), poly(D(+)-lactide) or a lactide-rich lactide/glycolide copolymer containing a lower molecular weight polymer or oligomer that is at least partially end-capped by a carboxylic acid group. The second absorbable polymer type is the absorbable polymer poly(p-dioxanone). The poly(p-dioxanone) may contain a lower molecular weight poly(p-dioxanone) that is at least partially end-capped by a carboxylic acid group.

It is to be understood that in the case of the lactide-rich lactide/glycolide copolymer, the lactide is ether substantially L(−)-lactide or D(+)-lactide; specifically avoiding meso-lactide or racemic-lactide, the latter a 50/50 blend of L(−)-lactide and D(+)-lactide. It is further understood that the stereocomplex made of poly(L(−)-lactide) and poly(D(+)-lactide) may be utilized, of any proportion, with the 50/50 mixture being particularly advantageous when high strength or high modulus is required. Further the lactide-rich lactide/glycolide copolymer may be a stereocomplex of a poly(L(−)-lactide-co-glycolide) and poly(D(+)-lactide-co-glycolide), of any proportion, with the 50/50 mixture again being particularly advantageous.

The first absorbable polymer type, made of the poly(L(−)-lactide), poly(D(+)-lactide), poly(L(−)-lactide)/poly(D(+)-lactide) stereocomplex, or a lactide-rich lactide/glycolide copolymer can comprise of a first amount of a polylactide or lactide-rich lactide/glycolide copolymer having a first weight-average molecular weight between about 40,000 Daltons to about 175,000 Daltons; and, a second amount of a polylactide or lactide-rich lactide/glycolide copolymer having a weight-average molecular weight of about 1,400 Daltons to about 24,000 Daltons, wherein at least one of those components is at least partially end-capped with a carboxylic acid; wherein a substantially homogeneous blend of the first and second amounts of the absorbable polymer is formed in a ratio of between about 50/50 to 99/1 weight/weight percent, and more preferably between about 78/22 to about 88/12.

The lactide-rich polymers can be typically synthesized using the procedure outlined in co-pending in U.S. 20120071566 A1 (which is incorporated by reference) with the exception of the choice of initiator. In the case of producing a high to moderate molecular weight, uncapped resin, a mono-alcohol such as dodecanol can be used; in the case of a high to moderate molecular weight, capped resin, one might also use a hydroxyacid such as lactic or glycolic acid, followed by capping the resulting resin. Alternately, for this later case, one might employ a diol initiator followed by the capping of one or both ends of the resulting polymer. Low molecular weight lactide-rich lactide/glycolide co-oligomer, or a low molecular weight lactide oligomer, oligolactide, may be made using a hydroxyacid such as lactic or glycolic acid, followed by capping the resulting oligomer, or employing a diol initiator followed by the capping of one or both ends of the resulting oligomer.

The first absorbable polymer type [the poly(L(−)-lactide), poly(D(+)-lactide), poly(L(−)-lactide)/poly(D(+)-lactide) stereocomplex, lactide-rich lactide/glycolide copolymer, or stereocomplex of poly(L(−)-lactide-co-glycolide) and poly(D(+)-lactide-co-glycolide)] will be manufactured in a conventional manner. A preferred manufacturing method is as follows:

a) Initially conducting a ring-opening polymerization (ROP) of an appropriate lactide monomer [L(−) or D(+), etc.] and glycolide monomer in the molar ratio of lactide to glycolide of 100/0 to 70/30 with the monomer to initiator ratio of about 300:1 to about 2,000:1.

b) Secondly conducting a ROP of an appropriate lactide monomer [L(−) or D(+), etc.] and glycolide monomers in the molar ratio of lactide to glycolide of 100/0 to 70/30 with the monomer to initiator ratio of about 10:1 to about 100:1. At the end of the polymerization reaction, a cyclic anhydride is added to the reactor in an amount that is equimolar to the amount of initiator used. After reacting for about 60 minutes, the resulting polymerization product is discharged from the reactor.

c) Blending the first and second components from steps a) and b) by either using a solvent or melt blending techniques with melt blending techniques preferred.

The blending of the first and second components from the above-described steps a) and b) can be done in the forming equipment used to make the device. Thus one might employ an injection molding machine to not only form a sought molded medical part, but to conduct step c), the blending. Likewise, a melt extruder might be used to not only form a sought extruded medical part, e.g. fiber or film, but to conduct step c), the blending.

The second absorbable polymer type can comprise a poly(p-dioxanone) with a unimodal molecular weight distribution or can comprise of two or more poly(p-dioxanone)s with different molecular weights. In the latter case, the second blend component may comprise: a first amount of a poly(p-dioxanone) polymer having a first molecular weight between about 42,000 Daltons to about 175,000 Daltons; and a second amount of a poly(p-dioxanone) polymer having a weight average molecular weight between about 1,400 Daltons to about 24,000 Daltons, wherein at least one of said components is at least partially end-capped with a carboxylic acid. A substantially homogeneous blend of the first and second amounts of the absorbable polymer is formed in a ratio of between about 50/50 to about 99/1 weight/weight percent.

The second absorbable polymer type is manufactured in a conventional manner as follows:

a) First conducting a ROP of p-dioxanone with a monomer to initiator ratio of about 300:1 to about 2,000:1 to result in a higher molecular weight poly(p-dioxanone).

b) Secondly conducting a ROP of p-dioxanone with a monomer to initiator ratio of about 10:1 to about 100:1 to result in a lower molecular weight poly(p-dioxanone). At the end of the polymerization reaction, a cyclic anhydride is added to the reactor in an amount that is equimolar to the amount of initiator used. After reacting for about 60 minutes, the resulting polymerization product is discharged from the reactor.

c) Blending the first and second p-dioxanone polymer components from steps a) and b) by either using a solvent or melt blending techniques with melt blending techniques preferred.

It is to be understood that one might advantageously reduce the number of (solution or melt) blending operations required by combining multiple blend components in a single blending procedure. For example, one might combine a higher molecular weight lactide-rich lactide/glycolide copolymer, a lower molecular weight acid end-capped lactide-rich lactide/glycolide copolymer and a higher molecular weight poly(p-dioxanone) in a single melt blending operation.

The following examples are illustrative of the principles and practice of the present invention, although not limited thereto.

Example 1

Synthesis of 85/15 Poly(L(−)-Lactide-co-Glycolide): Polymer of Normal Molecular Weight Distribution Into a suitable, conventional 15-gallon stainless steel oil jacketed reactor equipped with agitation, 43.778 kg of L(−)-lactide and 6.222 kg of glycolide were added along with 121.07 g of dodecanol and 9.02 mL of a 0.33M solution of stannous octoate in toluene. The reactor was closed and a purging cycle, along with agitation at a rotational speed of 12 RPM in an upward direction, was initiated. The reactor was evacuated to pressures less than 200 mTorr followed by the introduction of nitrogen gas to a pressure slightly in excess of one atmosphere. The cycle was repeated several times to ensure a dry atmosphere.

At the end of the final introduction of nitrogen, the pressure was adjusted to be slightly above one atmosphere. The vessel was heated at a rate of 180° C. per hour until the oil temperature reached approximately 130° C. The vessel was held at 130° C. until the monomer was completely melted and the batch temperature reached 110° C. At this point the agitation rotation was switched to the downward direction. When the batch temperature reached 120° C., the agitator speed was reduced to 7.5 RPM, and the vessel was heated using an oil temperature of approximately 185° C., with a heat up rate of approximately 60° C. per hour, until the molten mass reached 180° C. The oil temperature was maintained at approximately 185° C. for a period of 2.5 hours.

At the end of the reaction period, the agitator speed was reduced to 5 RPM, the oil temperature was increased to 190° C., and the polymer was discharged from the vessel into suitable containers for subsequent annealing. The containers were introduced into a nitrogen annealing oven set at 105° C. for a period of approximately 6 hours; during this step the nitrogen flow into the oven was maintained to reduce degradation due to moisture.

Once this annealing cycle was complete, the polymer containers were removed from the oven and allowed to cool to room temperature. The now crystallized polymer was removed from the containers, bagged, and placed into a freezer set at approximately −20° C. for a minimum of 24 hours. The polymer was removed from the freezer and placed into a conventional Cumberland granulator fitted with a sizing screen to produce polymer granules of approximately 3/16 inches in size. The granules were then sieved to remove any "fines" and then weighed. The net weight of the ground polymer was 39.46 kg, which was then placed into a 3 cubic foot conventional Patterson-Kelley tumble dryer.

The dryer was closed and the pressure was reduced to less than 200 mTorr. Once the pressure was below 200 mTorr, tumbler rotation was activated at a rotational speed of 8-15 RPM and the batch was vacuum conditioned for a period of 10 hours. After the 10 hour vacuum conditioning, the oil temperature was set to a temperature of 120° C., for a period of 32 hours. At the end of this heating period, the batch was allowed to cool for a period of at least 4 hours, while maintaining rotation and high vacuum. The polymer was discharged from the dryer by pressurizing the vessel with nitrogen, opening the slide-gate, and allowing the polymer granules to descend into waiting vessels for long term storage.

The long term storage vessels were air tight and outfitted with valves allowing for evacuation so that the resin was stored under vacuum. The resin was characterized. It exhibited an inherent viscosity of 1.79 dL/g, as measured in hexafluoroisopropanol at 25° C. at a concentration of 0.10 g/dL. Differential Scanning calorimetry (DSC) using the heating rate of 10° C./min revealed a glass transition temperature of 59° C. and a melting transition of 150° C., with the heat of fusion about 35 J/g. Nuclear magnetic resonance (NMR) analysis confirmed that the resin was a random copolymer of polymerized L(−)-lactide and glycolide, with a composition of about 85 percent polymerized L(−)-lactide and about 15 percent polymerized glycolide on a molar basis.

Example 2

Synthesis of a Capped Low Molecular Weight L/G Polymer, 85/15 Oligo(L(−)-lactide-co-glycolide)

Into a suitable, conventional 2-gallon stainless steel oil jacketed reactor equipped with agitation, 4,728.6 grams of L(−)-lactide and 671.5 grams of glycolide were added along with 204.63 g of diethylene glycol (DEG) as an initiator, and 0.97 ml of a 0.33M solution of stannous octoate in toluene. The reactor was closed to initiate a purging cycle, along with agitation at a rotational speed of 25 RPM in an upward direction. The reactor's pressure was reduced to 200 mTorr, and was held at this condition for 15 minutes, followed by the introduction of dry nitrogen gas. The cycle was repeated once again to ensure a dry atmosphere. At the end of the final introduction of nitrogen, the pressure was adjusted to be slightly above one atmosphere. Next, the heating oil temperature was raised to 130° C. at an average heating rate of 3° C./min. When the batch temperature reached 120° C., the agitator was stopped and restarted in the downward (reverse) direction at 20 RPM. The heating oil controller was then set at 185° C. at an average heating rate of 1° C. per minute. When the batch reached 180° C., the reaction was continued for an additional 3 hours and 30 minutes at 25 RPM while continuing to a nominal batch temperature of 185° C.

After running for three hours at 180° C. to 185° C., the agitator was stopped and 447.6 grams of diglycolic anhydride was added to the reactor. The agitation was continued for 60 minutes at 20 RPM in the downward direction. At the end of the reaction period, the polymer was discharged from the vessel into aluminum trays and stored in a freezer. Later, the polymer was ground using a conventional Cumberland grinder outfitted with a 3/16" screen. No drying procedure at elevated temperature was performed for this material.

The resin was stored under vacuum and subsequently characterized. It exhibited an inherent viscosity of 0.17 dL/g, as measured in hexafluoroisopropanol at 25° C. at a concentration of 0.10 g/dL. Differential Scanning calorimetry (DSC) using a heating rate of 10° C./min revealed a glass transition temperature of 38° C. No crystallinity was observed; this resin is however crystallizable if exposed to appropriate temperatures for appropriate times. Nuclear magnetic resonance (NMR) analysis confirmed that the resin was a random copolymer of polymerized L(−)-lactide and glycolide, with a composition of about 85 percent polymerized L(−)-lactide and about 15 percent polymerized glycolide on a molar basis.

Example 3

Synthesis of Poly(p-Dioxanone): Standard Molecular Weight Polymer

Into a suitable, conventional 65-gallon stainless steel oil jacketed reactor equipped with agitation, 164.2 kg of p-dioxanone monomer (PDO) was added along with 509 grams of dodecanol, 164 grams of D&C Violet No. 2 Dye, and 100 grams of a 0.33M solution of stannous octoate in toluene. The reactor was closed and a purging cycle, along with agitation at a rotational speed of 12 RPM in an upward direction, was initiated. The reactor was evacuated to pressures less than 500 mTorr followed by the introduction of nitrogen gas. The cycle was repeated several times to ensure a dry atmosphere.

At the end of the final introduction of nitrogen, the pressure was adjusted to be slightly above one atmosphere. The vessel was heated at a rate of 180° C. per hour until the oil temperature reached approximately 100° C. The oil temperature was held at 100° C. until the batch temperature reached 50° C., at which point the agitator rotation was changed to the downward direction. When the batch temperature reached 90° C., the oil temperature was reset to 95° C. These conditions were maintained, and samples were taken from the vessel to be measured for Brookfield viscosity. When the polymer batch viscosity reached at least 110 centipoise, the batch was ready for discharge. The agitator speed was reduced to 5 RPM, and a pre-heated filter was attached to the vessel discharge port. The polymer was discharged from the vessel into suitable containers, under a nitrogen purge, covered, and transferred into a nitrogen curing oven set at 80° C. A solid state polymerization was initiated for a period of approximately 96 hours; during this step the nitrogen flow into the oven was maintained to minimize degradation due to moisture.

Once the solid state curing cycle was complete, the polymer containers were removed from the oven and allowed to cool to room temperature. The crystallized polymer was removed from the containers, and placed into a freezer set at approximately −20° C. for a minimum of 24 hours. The polymer was removed from the freezer and ground in a conventional Cumberland granulator fitted with a sizing screen to reduce the polymer granules to approximately 3/16 inches in size. The granules were then sieved to remove any "fines" and then placed into a 20 cubic foot conventional Patterson-Kelley tumble dryer.

The dryer was closed and the pressure was reduced to less than 2 mmHg. Once the pressure was below 2 mmHg, dryer rotation was activated at a rotational speed of 6 RPM with no heat for 10 hours. After the 10 hour vacuum period, the oil temperature was set to 95° C. at a heat up rate of 120° C. per hour. The oil temperature was maintained at 95° C. for a period of 32 hours. At the end of this heating period, the batch was allowed to cool for a period of at least 4 hours, while maintaining rotation and vacuum. The polymer was discharged from the dryer by pressurizing the vessel with nitrogen, opening the discharge valve, and allowing the polymer granules to descend into waiting vessels for long term storage. The storage vessels were air tight and outfitted with valves allowing for evacuation so that the resin was stored under vacuum.

The resin was characterized. It exhibited an inherent viscosity of 1.90 dL/g, as measured in hexafluoroisopropanol at 25° C. and at a concentration of 0.10 g/dL. Differential Scanning calorimetry using a heating rate of 10° C./min revealed a glass transition temperature of about −8° C. (minus eight degrees Celsius), a melting transition at about 114° C., with a heat of fusion of about 88 J/g. Nuclear magnetic resonance analysis confirmed that the resin was the homopolymer poly(p-dioxanone), with a residual monomer content less than 2 percent.

Example 4

Preparation of a Ternary Blend Using the Capped L/G Oligomer of Example 2.

a) Dry Blends Preparation

Appropriate amounts of the 85/15 L/G copolymer of standard molecular weight distribution from Example 1, the Capped 85/15 L/G Oligomer from Example 2, and the poly(p-dioxanone) with standard molecular weight distribution from Example 3, all in divided form (ground), were combined in dry blends. The composition, on a weight basis, of these dry blends was selected depending on the particular application and surgical need. An example of a procedure is described directly below.

Into a clean 3-cubic foot conventional Patterson-Kelley dryer, 3,652 grams of granules of the 85/15 lactide/glycolide copolymer of Example 1, 748 grams of granules of the 85/15 lactide/glycolide capped oligomer of Example 2, and 1,100 grams of poly(p-dioxanone) with standard molecular weight distribution from Example 3 were added. The dryer was closed, and the vessel pressure was reduced to less than 200 MTorr. The rotation was started at 7.5 RPM and continued for a minimum period of one hour. The dry blend was then discharged into portable vacuum storage containers, and these containers were placed under vacuum, until ready for the melt blending step. Dried blends prepared in this study are listed in Table 2.

TABLE 2

Dry Inventive Blends Prepared in this Study with a Control without Capped Oligomer

| Sample ID | 85/15 L/G of EX. 1 (grams) | Poly(p-dioxanone) of EX. 3 (grams) | 85/15 L/G Capped Oligomer of EX. 2 (grams) | Wt. % of Poly(p-dioxanone) in final blend |
|---|---|---|---|---|
| 4A | 3,652 | 1,100 | 748 | 20 |
| 4B | 4,109 | 550 | 842 | 10 |
| 4C | 4,223 | 413 | 865 | 7.5 |
| 4D | 4,337 | 275 | 888 | 5 |
| 4E | 4,451 | 138 | 912 | 2.5 |
| 4F | 4,400 | 1,100 | 0 | 20 | b) Melt Blending of a Ternary Blend Using the Capped L/G Oligomer of Example 2

Once dry blends have been produced and have been vacuum conditioned for at least three days, they can be melt-blended. The dry blends of Examples 4A to 4F were melt-blended in the following way. A conventional ZSK-30 twin-screw extruder was fitted with screws designed for melt blending utilizing dual vacuum ports for purposes of volatilizing residual monomer. The screw design contained several different types of elements, including conveying, compression, mixing and sealing elements, as would be evident to one skilled in the art. The extruder was fitted with a three-hole die plate, and a chilled water bath with water temperature set between 40° F. and 70° F. was placed near the extruder outlet. A strand pelletizer and pellet classifier was placed at the end of the water bath. The extruder temperature zones were heated to temperatures of 160° C. to 180° C., and the vacuum cold traps were set to −20° C. The pre-conditioned dry blend granules were removed from vacuum and placed in a twin-screw feed hopper under nitrogen purge. The extruder screws were set to a speed of 175 RPM to 225 RPM, and the feeder was turned on, allowing the dry blend to be fed into the extruder.

The polymer melt blend was allowed to purge through the extruder until the feed was consistent, at which point the vacuum was applied to the two vacuum ports. The polymer blend extrudate strands were fed through the water bath and into the strand pelletizer. The pelletizer cut the strands into appropriate sized pellets; it was found that pellets with a diameter of 1 mm and an approximate length of 3 mm sufficed. The pellets were then fed into the classifier. The classifier separated substantially oversized and undersized pellets from the desired size, usually a weight of about 10-15 mg per pellet. This process continued until the entire polymer dry blend was melt blended in the extruder, and formed into substantially uniform pellets. Samples were taken throughout the extrusion process and were measured for polymer characteristics such as inherent viscosity, molecular weight and composition. Once the melt-blending process was completed, the pelletized polymer was placed in polyethylene bags, weighed, and stored in a freezer below −20° C. to await devolatilization of residual monomer.

The polymer melt-blends were then placed into a 3-cubic foot conventional Patterson-Kelley dryer, which was placed under vacuum. The dryer was closed and the pressure was reduced to less than 200 mTorr. Once the pressure was below 200 mTorr, dryer rotation was activated at a rotational speed of 10 RPM with no heat for 6 hours. After the 6 hour period, the oil temperature was set to 85° C. at a heat up rate of 120° C. per hour. The oil temperature was maintained at 85° C. for a period of 12 hours. At the end of this heating period, the batch was allowed to cool for a period of at least 4 hours, while maintaining rotation and vacuum. The polymer melt-blend pellets were discharged from the dryer by pressurizing the vessel with nitrogen, opening the discharge valve, and allowing the polymer pellets to descend into waiting vessels for long term storage. The storage vessels, outfitted with valves allowing for evacuation, and being air tight, allowed the inventive resin blend to be stored under vacuum.

The inventive resin blends were characterized. Nuclear Magnetic Resonance (NMR) analysis confirmed that the blends were properly mixed in required weight amounts, with residual monomer content for all blends less than 1 percent. The blends were examined for an inherent viscosity, where samples were measured in hexafluoroisopropanol at 25° C. and at a concentration of 0.10 g/dL. The resulting melt blend compositions were subjected to melt viscosity measurements using a melt flow index apparatus (MT987 Extrusion Plastometer, Tinius Olsen, Willow Grove, Pa., USA). The measurements were conducted at 190° C. using a 6,600 g weight disc. The die diameter was 0.0260 inches, while the die length was 0.315 inches. The results for inherent viscosity (IV), and Melt Flow Index (MFI), are summarized in Table 3.

TABLE 3

Melt Flow Index and Inherent Viscosity Data for Inventive Blends and a Control without Capped Oligomer Component

| Sample ID | Wt. % of PDS in blend | MFI (g/10 min) | IV (dL/g) |
|---|---|---|---|
| 4A | 20 | 0.268 | 1.40 |
| 4B | 10 | 0.204 | 1.37 |
| 4C | 7.5 | 0.200 | 1.44 |
| 4D | 5 | 0.182 | 1.46 |
| 4E | 2.5 | 0.202 | 1.46 |
| 4F | 20 | 0.115 | 1.74 |

Example 5

Calorimetric Evaluation of Inventive Blends Compositions

Differential Scanning calorimetry (DSC) was also used to investigate the thermal transitions and crystallization kinetics of blend compositions, both inventive blends of the present invention and a control. The following methods/conditions were used:

a) First heat measurements—a 5 to 8 milligram sample of interest was quenched to −60° C. [minus 60 degrees Celsius] in a DSC pan equipped with nitrogen purge, followed by the constant heating rate scan of 10° C./min b) Second heat measurements—the sample of interest after melting in a DSC pan at 185° C., and followed by a rapid quench (−60° C./min) to −60° C. was then heated at the constant heating rate of 5° C./min to 185° C.

A summary of DSC results obtained on pellets of a control and blends of the present invention can be found in Table 4 below. The pellets underwent elevated temperature devolatilization that should have been sufficient to develop a nearly maximum level of crystallinity. This would be reflected in the "first heat" results. The "second heat" results reflect the inherent crystallization properties of the test samples because the thermal history would have been erased, as is well known to those skilled in the art.

TABLE 4

DSC Calorimetric Properties of a Control and of Inventive Dried Capped Oligomer Containing Blends

| Blend ID | Comments | First Heat Data (10° C./min) | | | Second Heat Data (5° C./min) | | |
|---|---|---|---|---|---|---|---|
| | | $T_g$ (° C.) | $T_m$ (° C.) | $\Delta H_m$ (J/g) | $T_g$ (° C.) | $T_m$ (° C.) | $\Delta H_m$ (J/g) |
| 4F | 80 wt. % 85/15 Lac/Gly Copolymer+ 20% of Poly(p-dioxanone), PDS (control, non-inventive) | 55.8 | 148 | 26.1 | 55.2 | 151 | 1.0 |
| 4A | Blend of 66.4 wt. % of the Copolymer of EX. 1, + 13.6 wt. % of the Capped Oligomer of EX. 2, + 20 wt. % PDS | 55.1 | 147 | 24.8 | 53.2 | 150 | 0.5 |

TABLE 4-continued

DSC Calorimetric Properties of a Control and of Inventive Dried Capped Oligomer Containing Blends

| Blend ID | Comments | First Heat Data (10° C./min) | | | Second Heat Data (5° C./min) | | |
|---|---|---|---|---|---|---|---|
| | | $T_g$ (° C.) | $T_m$ (° C.) | $\Delta H_m$ (J/g) | $T_g$ (° C.) | $T_m$ (° C.) | $\Delta H_m$ (J/g) |
| 4B | Blend of 74.7 wt. % of the Copolymer of EX. 1, + 15.3 wt. % of the Capped Oligomer of EX. 2, + 10 wt. % PDS | 54.7 | 147 | 25.8 | 52.9 | 150 | 0.4 |
| 4D | Blend of 78.9 wt. % of the Copolymer of EX. 1, + 16.1 wt. % of the Capped Oligomer of EX. 2, + 5 wt. % PDS | 53.7 | 148 | 26.6 | 52.2 | 150 | 0.5 |
| 4E | Blend of 80.9 wt. % of the Copolymer of EX. 1, + 16.6 wt. % of the Capped Oligomer of EX. 2, + 2.5 wt. % PDS | 55.2 | 147 | 19.3 | 52.5 | 150 | 0.4 |

Example 6A

Figure 5:
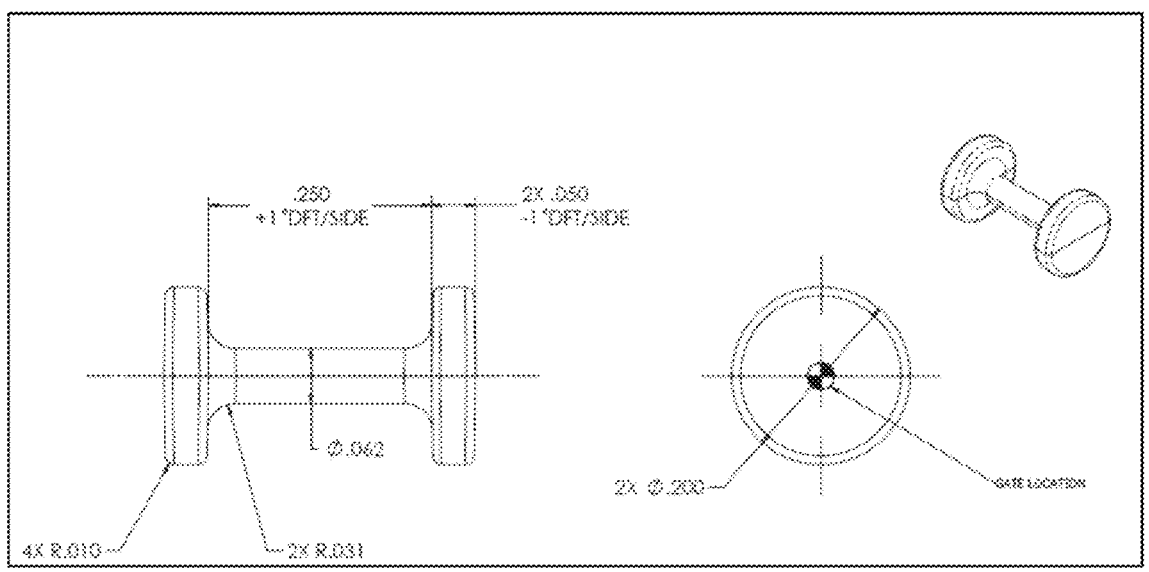
FIG. 5 is a drawing of a dumbbell test article.

Injection Molding of Control Polymers and Blends, and Inventive Bimodal Blends into Straps and Dumbbells Injection molding is a process well known in the plastic industry. It is designed to produce parts of various shapes and sizes by melting the plastic resin, mixing and then injecting the molten resin into a suitably shaped mold. For the purpose of this invention, two injection molding shapes were explored: straps and dumbbells. These shapes are shown in FIGS. 1 and 5, respectively. After the resin is solidified, the part is generally ejected from the mold and the process continued. For the purposes of this invention, a conventional 30-ton electrically controlled injection molding machine was used. The polymers and blends of Examples 1 and 6 were processed by the injection molding machine in the following general manner.

The polymer was fed by gravity from a hopper, under nitrogen purge, into a heated barrel and allowed to melt. The polymer was moved forward in the barrel by a screw-type plunger, eventually into a heated chamber in front of the screw at the distal end of the barrel. The screw was then advanced forward in a translational motion, which forced the molten polymer through a nozzle that sat against the mold, allowing the polymers to enter a specially designed mold cavity, through a gate and runner system. The polymer was formed into the part in the mold cavity, and allowed to cool at a given temperature for a period of time. The part was then removed from the mold, or ejected, and separated from the runner.

The injection molding cycle consisted of the entire series of events during the process. It began when the mold closed, and was followed by the injection of the molten polymer into the mold cavity. Once the cavity was filled, hold pressure was maintained to compensate for material shrinkage. Next, the screw-plunger turned and retracted, feeding the next "shot" to the front of the screw. While preparing the next shot in the barrel, the part in the mold was cooled to sufficient temperature, and the mold opened and the part was ejected. The next cycle initiated upon the closing of the mold. The cycle times ranged from about 25 seconds to about 75 seconds and were based on a number of factors, including part size and material composition.

Example 6B

Annealing Molded Parts

The injection molded articles of Example 6A were then subjected to a thermal annealing cycle to mature the polymer morphology. The articles in Example 6A were annealed using an annealing fixture that supported the parts from distortion within the horizontal plane of the part. Although this annealing fixture is intended to aid in the resistance of distortion at elevated temperatures during annealing, it will not prevent dimensionally unstable parts from warping. The annealing cycle used for the articles in Example 6A was composed of three steps: 60° C. for 8 hours, 70° C. for 4 hours, and then 80° C. for 4 hours. The purpose of the 60° C. step is to further crystallize the poly(p-dioxanone) phase in the blend before reaching the crystallization temperatures for the poly(lactide-co-glycolide) phase. The 70° C. step begins to crystallize the poly(lactide-co-glycolide) phase before reaching the last step in the cycle. Finally, the 80° C. step further crystallizes the poly(lactide-co-glycolide) phase. It should be noted that for a given device and given composition annealing conditions may be found that optimize certain important performance characteristics. These advantageous annealing conditions can be developed through experimentation, changing the annealing temperature and annealing duration, and measuring the response.

Once the injection parts of Example 6A were annealed, they were identified as the annealed parts of Example 6B.

Example 7

Calorimetric Properties of Annealed Dumbbells

Calorimetric data was obtained utilizing Differential Scanning calorimetry (DSC), at a heating rate of 10° C./min with a sample weight of 5 mg to 8 mg on a number of annealed dumbbells (DB). These include samples based on: a control blend of 80 weight percent 85/15 L/G copolymer and 20 weight percent PDS [Sample DB 6A]; the neat 85/15 L/G copolymer of Example 1 [DB 6B]; the inventive blend of 66.4 weight percent 85/15 L/G copolymer, 13.6 weight percent 85/15 L/G capped oligomer and 20 weight percent PDS [DB 6C]; as well as the inventive blends ranging in composition of 74.7 to 80.9 weight percent 85/15 L/G copolymer of bimodal molecular weight distribution, 15.3 to 16.6 weight percent 85/15 L/G Capped oligomer, and 2.5 to 10 weight percent PDS of normal molecular weight distribution [Samples DB 6D, DB 6E, and DB 6F, respectively]. The DSC results obtained on annealed dumbbells (center section) made from these various blends are summarized in Table 5 below.

TABLE 5

Calorimetric (DSC) Properties of Annealed[1] Dumbbells of an 85/15 L/G Copolymer Control, a Prior Art Blend Control, and the Blends of the Present Invention Based on a Capped Oligomeric Component

| | | DSC First Heat Data (10° C./min) | | | |
|---|---|---|---|---|---|
| Dumbbell Sample ID | Comments | $T_g$ [PDS] (° C.) | $T_g$ [Lactide-Based Copolymer] (° C.) | $T_m$ (° C.) | $\Delta H_m$ (J/g) |
| DB 6A | Control From Prior Art, a blend of 80% 85/15 L/G + 20% PDS | −19.6 | 46.3 | 102/ 147 | 28.9 |
| DB 6B | 85/15 L/G Copolymer of Example 1 | NA | 53.5 | 148 | 26.5 |
| DB 6C | Blend of 66.4 wt. % of the Copolymer of EX. 1, + 13.6 wt. % of the | −14.2 | 47.1 | 104/ 147 | 29.6 |

TABLE 5-continued

Calorimetric (DSC) Properties of Annealed[1] Dumbbells of an 85/15 L/G Copolymer Control, a Prior Art Blend Control, and the Blends of the Present Invention Based on a Capped Oligomeric Component

| Dumbbell Sample ID | Comments | DSC First Heat Data (10° C./min) | | | |
|---|---|---|---|---|---|
| | | $T_g$ [PDS] (° C.) | $T_g$ [Lactide-Based Copolymer] (° C.) | $T_m$ (° C.) | $\Delta H_m$ (J/g) |
| DB 6D | Capped Oligomer of EX. 2, + 20 wt. % PDS Blend of 74.7 wt. % of the Copolymer of EX. 1, + 15.3 wt. % of the Capped Oligomer of EX. 2, + 10 wt. % PDS | −14.9 | 49.8 | 104/ 148 | 30.0 |
| DB 6E | Blend of 78.9 wt. % of the Copolymer of EX. 1, + 16.1 wt. % of the Capped Oligomer of EX. 2, + 5 wt. % PDS | −13.9 | 48.9 | 105/ 148 | 28.7 |
| DB 6F | Blend of 80.9 wt. % of the Copolymer of EX. 1, + 16.6 wt. % of the Capped Oligomer of EX. 2, + 2.5 wt. % PDS | Not detected | 50.1 | 102/ 148 | 29.5 |

[1]Annealing conditions: 60° C. for 8 hrs, followed by 70° C. for 4 hrs, followed by 80° C. for 4 hrs The DSC results shown in Table 5 above allow for the following conclusions. The glass transition temperature of PDS was identified in those blends containing this component at a 5 weight percent or greater level. This is indicative of a phase separated morphology. The melting behavior resulted in the observation of two melting transition temperatures, $T_{m1}$ and $T_{m2}$, although overlapping, in those articles based on blends of 85/15 L/G copolymer and PDS. One of these melting transitions temperatures corresponded to PDS and one corresponded to the L/G copolymer. The PDS-based meltings ranged from 102° C. to 105° C., while the L/G-based melting ranged from 147° C. to 148° C. The presence of these two endotherms and the fact that they remain fairly invariant with regard to temperature even though the relative amounts of the blend components vary is further indicative of the phase separated morphology. The combined heats of melting, $\Delta H_m$ of the two melting endotherms is reported in the last column of Table 5. It is well established that that the heat of fusion is proportional to the crystallinity level of the part. We can thus model the crystallinity level by following the $\Delta H_m$.

It is noted that all the annealed molded dumbbells prepared from the resins based on ternary blends of L/G copolymer, L/G capped oligomer, and PDS listed in Table 5 exhibited higher $\Delta H_m$ values when compared to the L/G copolymer alone [Sample DB 6B]. These higher $\Delta H_m$ values imply an expected higher crystallinity levels. It was also found that all inventive ternary blends (Samples 6C, 6D, 6E, and 6F) exhibited $\Delta H_m$ values that are comparable or slightly higher than that exhibited by the normally distributed control of Sample DB 6A.

Example 8

Evaluation of Stiffness and Strength of Annealed Dumbbells

There are advantages to minimizing the amount of PDS in a blend. These include producing articles that are stiffer and that are stronger; the mechanical strength retention post-implantation of articles prepared therefrom would also be extended with lower levels of PDS blend component.

The annealed dumbbells were tested on a mechanical tester, Instron Model 5544 (Norwood, Mass., USA), using a 100 lbs. load cell. All instruments were up-to-date on calibration at the time of testing. The specimens were loaded in tension at a rate of 0.5 in/min until fracture. The maximum force was recorded as the tensile strength of the specimen. The Young's Modulus was calculated as the slope of the line linking two points located on the linear region of the force-extension curve of the test specimen. The following formula was utilized:

$$E = (\Delta F/A_0)/(\Delta L/L_0)$$

where E is the calculated Young's Modulus, $\Delta F$ is the change in force measured at the selected points, $A_0$ is the initial cross-sectional area of the specimen, $\Delta L$ is the change in cross-head displacement at selected points and $L_0$ is the gage length of the specimen. The initial cross-sectional area and the gage length considered in the calculations are $2.83 \times 10^{-3}$ in$^2$ and 0.25 inches, respectively.

The brief summary of tensile properties obtained in this study is given in Table 6 below.

TABLE 6

Tensile Strength and Young's Modulus (Stiffness) Data for Selected Annealed Dumbbell Samples made from a Control and the Inventive Blends made using Capped Oligomer

| Sample ID | Comments | Max Load (lbf) | SDEV | Young's Modulus (kpsi) | SDEV |
|---|---|---|---|---|---|
| DB 6A | Control From Prior Art, a blend of 80% 85/15 L/G + 20% PDS | 26.30 | 1.68 | 130.3 | 4.81 |
| DB 6C | Blend of 66.4 wt. % of the Copolymer of EX. 1, + 13.6 wt. % of the Capped Oligomer of EX. 2, + 20 wt. % PDS | 25.30 | 2.29 | 125.9 | 4.68 |
| DB 6D | Blend of 74.7 wt. % of the Copolymer of EX. 1, + 15.3 wt. % of the Capped Oligomer of EX. 2, + 10 wt. % PDS | 26.16 | 0.99 | 137.9 | 5.78 |
| DB 6E | Blend of 78.9 wt. % of the Copolymer of EX. 1, + 16.1 wt. % of the Capped Oligomer of EX. 2, + 5 wt. % PDS | 27.72 | 0.61 | 142.5 | 3.38 |
| DB 6F | Blend of 80.9 wt. % of the Copolymer of EX. 1, + 16.6 wt. % of the Capped Oligomer of EX. 2, + 2.5 wt. % PDS | 28.43 | 0.62 | 145.9 | 4.72 |

The mechanical property data generated and summarized in Table 6 show that for the same level of poly(p-dioxanone) present in the blend, dumbbells made from the inventive blends of the present invention are less stiff that the control blend (see Sample DB 6A versus Sample DB 6C). With decreasing PDS content, however, dumbbells made from the inventive blends become increasingly stronger and stiffer.

Example 9

In vitro Hydrolysis Data of Annealed Dumbbells

The hydrolysis data was collected on the same annealed dumbbell samples as were used to collect the mechanical property data generated and summarized in Table 6 above. The methodology employed is similar to that described in U.S. patent application 2013/0330827 A1, entitled "In vitro methodology for predicting in vivo absorption time of bioabsorbable polymeric implants and devices", which is incorporated by reference. Here, data was collected using automatic titrations at 70° C. in phosphate buffer at a pH of 7.27 and is summarized in Table 7 below.

TABLE 7

The Time to Achieve 10, 50, and 90 Percent Hydrolysis of the Ester Groups In Various Annealed Dumbbells in vitro at 70° C. in Phosphate Buffer at a pH of 7.27

| Sample ID | Comments | $t_{10\%}$ (hrs) | $t_{50\%}$ (hrs) | $t_{90\%}$ (hrs) |
|---|---|---|---|---|
| DB 6A | Control From Prior Art, a blend of 80% 85/15 L/G + 20% PDS | 25 | 156 | 287 |
| DB 6C | Blend of 66.4 wt. % of the Copolymer of EX. 1, + 13.6 wt. % of the Capped Oligomer of EX. 2, + 20 wt. % PDS | 21 | 124 | 272 |
| DB 6D | Blend of 74.7 wt. % of the Copolymer of EX. 1, + 15.3 wt. % of the Capped Oligomer of EX. 2, + 10 wt. % PDS | 30 | 133 | 284 |
| DB 6E | Blend of 78.9 wt. % of the Copolymer of EX. 1, + 16.1 wt. % of the Capped Oligomer of EX. 2, + 5 wt. % PDS | 39 | 161 | 395 |
| DB 6F | Blend of 80.9 wt. % of the Copolymer of EX. 1, + 16.6 wt. % of the Capped Oligomer of EX. 2, + 2.5 wt. % PDS | 44 | 169 | 363 |

A number of conclusions can be drawn from the hydrolysis data of Table 7 above. For instance, for the same amount of PDS (20%), the dumbbell made from capped oligomer containing blend (Sample DB 6C) hydrolyzed faster than a dumbbell made from the control blend (Sample DB 6A).

With decreasing PDS content, capped oligomer containing dumbbells become increasingly longer to absorb. Then to achieve a faster hydrolysis time, it was found that some of the L/G copolymer could be replaced by capped L/G oligomer. For instance, one might utilize the inventive blend based on the components of 74.7 weight percent of the 85/15 L/G copolymer (such as that of EX. 1), 15.3 weight percent of capped 85/15 L/G oligomer (such as that of EX. 2), and 10 weight percent PDS, instead of the blend based on the components of 90 weight percent of the 85/15 L/G copolymer (such as that of EX. 1), and 10 weight percent PDS. To be clear, the presence of the capped oligomer shortens hydrolysis time.

Example 10

In Vitro Breaking Strength Retention (BSR) Data of Annealed Dumbbells

In vitro breaking strength retention data was collected on the same annealed dumbbell samples used to collect the mechanical property data generated and summarized in Table 6 above, as well as the in vitro hydrolysis data summarized in Table 7 above. To be clear, the data is directed towards the loss of mechanical properties with time; in this case tensile strength was followed. In vitro breaking strength retention data was collected at room temperature after incubation at 37° C. in phosphate buffer at a pH of 7.27; again, the data are summarized in Table 8 below.

TABLE 8

Tensile Strength Remaining in Various Annealed Dumbbells after Incubation in vitro at 37° C. in Phosphate Buffer at a pH of 7.27

| Sample ID | 0 day (lbs)/ (SDEV) | 14 day (lbs)/ (SDEV) | 14 day (%) | 28 day (lbs)/ (SDEV) | 28 day (%) | 56 day (lbs)/ (SDEV) | 56 day (%) |
|---|---|---|---|---|---|---|---|
| DB 6A | 28.1/ (1.85) | 12.0/ (1.56) | 42.7 | 7.78/ (2.08) | 27.7 | 4.90/ (2.06) | 17.4 |
| DB 6C | 25.3/ (2.25) | 6.72/ (2.35) | 26.6 | 3.83/ (1.41) | 15.1 | 1.93/ (0.72) | 7.62 |
| DB 6D | 27.5/ (1.29) | 9.01/ (1.28) | 32.8 | 3.16/ (1.30) | 11.5 | 1.06/ (0.43) | 3.86 |
| DB 6E | 29.2/ (0.84) | 5.54/ (1.46) | 19.0 | 1.08/ (0.62) | 3.70 | 0.25/ (0.12) | 0.86 |
| DB 6F | 29.9/ (0.35) | 0.86/ (0.77) | 2.87 | 0.23/ (0.07) | 0.77 | 0.06/ (0.03) | 0.20 |

A number of conclusions can be drawn from the "strength remaining" data depicted in Table 8 above. The "Zero Day" (0 day) or baseline strength increased with lower PDS content. At fixed 20% PDS level, however, the annealed dumbbells based on the blend containing capped oligomer were found to exhibit a much faster loss of mechanical properties than the corresponding annealed dumbbells based on the blend without the capped oligomer. Specifically, annealed dumbbells DB 6A, the control articles, exhibited approximately 43, 28, and 17 percent strength remaining after 14, 28 and 56 days of incubation, respectively. In contrast to this, the annealed dumbbells of DB 6C, having the same 20 weight percent of PDS as the control samples, DB 6A, exhibited approximately 27, 15 and 8 percent strength remaining after 14, 28 and 56 days of incubation, respectively.

In examining the data of Table 8, the surprising and unexpected result was observed that breaking strength retention significantly decreased with lower PDS content. Test articles made from blends of high lactide, lactide/glycolide copolymers (or polylactide homopolymer) with poly(p-dioxanone) usually retain breaking strength better at lower PDS levels; the inventive blend behavior is in surprising conflict with this.

There are opportunities and needs for absorbable injection molded surgical devices that display dimensional stability that are stiffer than the prior art. There are other opportunities and needs for like devices that absorb at a faster rate than those of the prior art. Finally, there are other opportunities and needs for like devices that lose their strength at a much faster rate than those of the prior art. The inventive devices and the blends of the present invention satisfy these needs.

Example 11

Dimensional Stability

The injection molded articles of Examples 6A and 6B [that is molded articles before and after annealing] in the form of straps (AKA tacks or staples; see FIGS. 1 and 2) were tested for dimensional stability. The dimensions of the molded articles were measured prior to annealing and after annealing; additionally, photographic images were taken [see FIG. 6 to FIG. 9]. Although it is not expected to have all dimensions match exactly, it is clear that certain dimensions are critical to the functioning of the device. In some of the cases unacceptable levels of distortion were found; the inventive articles made from the inventive blends however displayed acceptable dimensional stability.

The test articles of Examples 6A and 6B in the form of straps are geometrically complex and have a number of critical dimensions. For instance, if the legs of the molded article distort excessively, the ability of the device to penetrate and hold tissue will be reduced. Likewise, if the barbs of the molded article were to shrink significantly, functionality would be reduced because of diminished ability to hold tissue. Every design will have its own critical dimensions. It is believed that the design of the straps of Examples 6A and 6B is representative of a demanding device regarding dimensional stability; this is felt in part because of geometric complexity and because of the expected high shear generated during molding of these small parts. That is, the fine part size will tend to increase molecular orientation during injection molding leading to an increased driving force for distortion of the ejected part [that is the part after removal from the mold cavity] at elevated temperatures as seen in annealing, and/or sterilization, and/or storage. Parts were evaluated and characterized in a "pass/fail" manner. Disposition of the molded articles were based on gross warping effects, of which an article was considered to have passed if excessive distortion was not evident. Likewise, if excessive distortion was evident, the part was said to have failed. Inherently, all injection molded articles have some degree of residual stress after molding, so parts that display tolerable levels of distortion are said to have passed the dimensional stability test. For the articles of Examples 6A and 6B, the tip-to-tip distance is a critical dimension; see FIG. 1.

FIG. 2 is a drawing of the device of FIG. 1 showing the critical dimensions of said device. These dimensions, if changed by lack of dimensional stability, can lead to poor performance and or a failure of the device. A tip-to-tip distance of less than 0.115 inches for the strap articles of Examples 6A and 6B was said to be acceptable, while a tip-to-top distance greater than or equal to 0.115 inches was said to be unacceptable and denoted as "failure mode one" or "fm1". Likewise, the lengths of the barb members from the straps of Examples 6A and 6B were also considered critical dimensions. A barb length of less than or equal to 0.136 inches was considered unacceptable and denoted as "failure mode 2" or "fm2". The photographic images and dimensions were captured using a Keyence digital microscope, model VHX-600, with a magnification of 20×. A summary of the test results is shown in Table 9 below.

TABLE 9

Calorimetric (DSC) Properties of Annealed[1] Control Straps and Corresponding Straps Made from Blends with Capped Olgomeric Component.

| | | First Heat Data (10° C./min) | | | | |
|---|---|---|---|---|---|---|
| EXAMPLE | Comments | $T_g$ [PDS Based] (° C.) | $T_g$ [L/G Copolymer Based] (° C.) | $T_m$[2] (° C.) | $\Delta H_m$ (J/g) | Dimensional Stability |
| Straps Based on a Lactide/Glycolide Copolymer ONLY- Example 1 | | | | | | |
| STR 11-1 | Unimodal 85/15 L/G Copolymer (Control 1) | Molded parts failed to hold shape, sticking issues, and distortions were observed | | | | |
| Straps Based on Blends in Which the Blend Components are: | | | | | | |
| STR 11-2 | Prior Art Blend of 80% Unimodal 85/15 L/G Copolymer and 20% PDS (Control 2) | −9.8 | 52.6 | 103/148 | 33.6 | YES |
| Straps Based on Blends in Which the Lactide-Based Part Has Capped Olgiometric Component: | | | | | | |
| STR 11-3 | Blend of 80.9% EX. 1, 16.6% EX. 2, and 2.5% PDS | −7.0 | 51.5 | 148 | 21.2 | NO |
| STR 11-4 | Blend of 76.8% EX. 1, 15.7% EX. 2, and 7.5% PDS | −13.3 | 48.6 | 104/146 | 30.7 | NO |
| STR 11-5 | Blend of 74.7% EX. 1, 15.3% EX. 2, and 10% PDS | −10.5 | 49.2 | 104/147 | 31.2 | YES |
| STR 11-6 | Blend of 66.4% EX. 1, 13.6% EX. 2, and 20% PDS | −7.6 | 48.4 | 104/146 | 37.5 | YES |

[1]Analysis conducted on the crown portion of an annealed molded strap. The annealing conditions employed were 60° C. for 8 hours followed by 70° C. for 4 hours followed by 80° C. for 4 hours.
[2]Listed herein are two values; the first is represents the meling poing of PDS-based blend component and the second value respresents the melting point observed for the lactide-based blend compnent.

In Table 9 above, the calorimetric properties of annealed straps of Examples 6B are provided along with the results of dimensional stability testing. The calorimetric data is a result of DSC (first heat) testing as described earlier in this application. The "first heat" DSC measurements were used to calculate the heats of fusion, $\Delta H_m$ (J/g), of the annealed straps [see Example 6B]. These values are directly proportional to the relative crystallinity level present in the test articles.

The annealed articles shown in Table 9 are of three varieties. In one case, the annealed straps are based on blends in which the blend components are without capped oligomeric component, [Sample STR 11-2]. In a second case, the annealed straps are based on a lactide/glycolide copolymer of Example 1 only, [STR 11-1]. The third variety represents a series of ternary blends containing different amount of capped oligomeric component [Samples STR 11-3, STR 11-4, STR 11-5, and STR 11-6]; the level of the minor blend component, poly(p-dioxanone), was 2.5, 7.5, 10 or 20 weight percent.

An examination of the strap articles of Example STR 11-1 was performed. These articles are based on an 85/15 lactide/Glycolide copolymer only. The strap articles of Sample STR 11-1 acted as a control group—Control 1. Although the articles exhibited crystallinity after annealing, the molded parts failed to hold shape during this process; they were dimensionally unstable with significant distortions being observed.

The injection molded straps of Example STR 11-2 are based on the prior art blend of 80% (unimodal molecular weight distribution) 85/15 L/G copolymer and 20% PDS and represent a second control group—Control 2. As expected, these articles exhibited dimensional stability. Dimensional stability is provided by the presence of 20 weight percent of poly(p-dioxanone). The annealed straps of Example STR 11-2 exhibited a $\Delta H_m$ of 33.6 J/g, indicative of a significant level of crystallinity. The presence of the poly(p-dioxanone) blend component does, however, decrease the stiffness of the article. Minimizing the amount of poly(p-dioxanone) present in the blend would lead to stiffer articles which in certain applications would be advantageous. To achieve dimensional stability in finely detailed molded articles, however, it has been shown in the prior art that a minimum of about 12.4 weight percent of poly(p-dioxanone) is required.

The injection molded straps of Samples STR 11-3 to STR 11-6 are based on blends in which the capped oligomeric 85/15 L/G component is present. Specifically, these were ternary blends made from 85/15 L/G copolymer of standard molecular weight ranging from 66.4 wt. % to 80.9 wt. %, blended with 85/15 L/G capped oligomer ranging from 13.6 wt. % to 16.6 wt. %, and blended with standard molecular weight PDS, in which the latter polymer is present at 2.5, 7.5, 10 and 20 weight percent, respectively. The inventive articles of Samples STR 11-5 and STR 11-6 exhibited dimensional stability; this corresponds to PDS being present at the 10 and 20 weight percent level, respectively. Based on the calorimetric data of Table 9, these two annealed straps made from inventive ternary blends, exhibited relatively high levels of crystallinity. Note that the annealed strap of Sample STR 11-5 was made with only 10 weight percent PDS, yet exhibited a $\Delta H_m$ of 31.2 J/g, close to the 33.6 J/g value exhibited by Control 2, Sample STR 11-2, made with twice the amount of PDS blend component, 20 percent. The corresponding straps made with 2.5 and 7.5 weight percent PDS did not exhibit dimensional stability as noted in Table 9; in both of these cases, the level of crystallinity is lower as evidenced by the lower $\Delta H_m$ values: 21.2 J/g and 30.7 J/g, respectively. Dimensional stability was found to be dependent on the $\Delta H_m$ (or crystallinity) of the article; when the annealed article exhibited a $\Delta H_m$ of greater than about 31 J/g, the article tended to be dimensionally stable.

Figure 6:
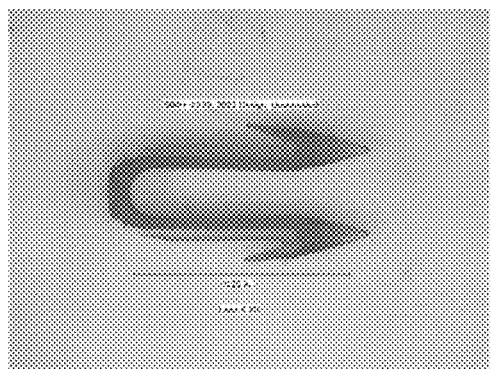
FIG. 6 is a photograph of an injection molded tack of Sample STR 11-4 prior to annealing made from the polymer composition of Example 4b having 7.5 weight percent poly(p-dioxanone).
Figure 7:
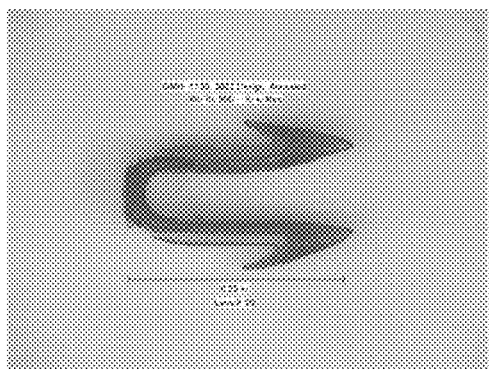
FIG. 7 is a photograph of an injection molded tack of Sample STR 11-4 after annealing, made from the polymer composition of Example 4b having 7.5 weight percent poly(p-dioxanone), said injection molded tacks exhibiting unacceptable warping after annealing.

Further evidence of dimensional stability or instability is presented in the photographs of FIG. 6 to FIG. 9 where the injection molded straps made from the composition of Example 6B having 7.5 or 10 weight percent poly(p-dioxanone) blend component are depicted. FIG. 6 is a photograph of an injection molded tack of Sample STR 11-4 prior to annealing made from the polymer composition of Example 6B having 7.5 weight percent poly(p-dioxanone); FIG. 7 is a photograph of an injection molded tack of Sample STR 11-4 after annealing made from the polymer composition of Example 6B having 7.5 weight percent poly(p-dioxanone); these injection molded tacks exhibited unacceptable warping after annealing.

Figure 8:
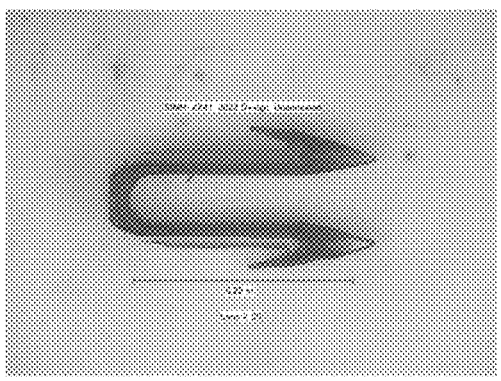
FIG. 8 is a photograph of an injection molded tack of Sample STR 11-5 prior to annealing made from the polymer composition of Example 4b having 10 weight percent poly(p-dioxanone).
Figure 9:
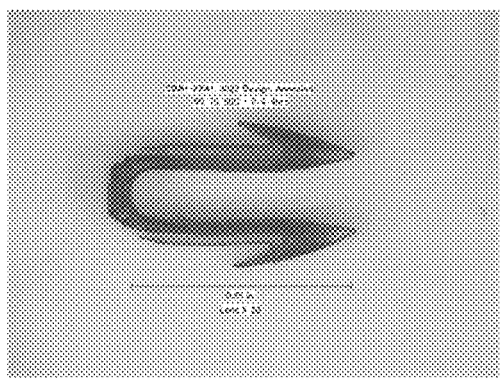
FIG. 9 is a photograph of an injection molded tack of Sample STR 11-5 after annealing, made from the polymer composition of Example 4b having 10 weight percent poly(p-dioxanone), said injection molded tacks exhibiting superior dimensional stability and an acceptable level of warping after annealing.

FIG. 8 is a photograph of an injection molded tack of Sample STR 11-5 prior to annealing made from the polymer composition of Example 6B having 10 weight percent poly(p-dioxanone); FIG. 9 is a photograph of an injection molded tack of Sample STR 11-5 after annealing made from the polymer composition of Example 6B having 10 weight percent poly(p-dioxanone); these injection molded tacks exhibited superior dimensional stability and an acceptable level of warping after annealing.

Returning to the data presented in Table 9, one finds that in the case of the annealed straps of Samples STR 11-3 to 11-6, two separate glass transition phenomena and two separate melting endotherms were observed. These corresponded to the poly(p-dioxanone) [PDS] blend component and the lactide-based blend components (the corresponding polymeric and the capped oligomeric components). The observation of two glass transition temperatures is universally accepted supportive evidence of component immiscibility. All poly(p-dioxanone)-based glass transition temperatures were between about −7° C. and about −13° C., while the glass transition temperatures associated with the lactide-rich-based blend components were between about 48° C. and about 53° C.

Two melting points were observed in the annealed injection molded articles made from the various blends shown in Table 9. The observation of two melting points is evidence that each blend component was crystallizable and was semicrystalline in the annealed articles. All poly(p-dioxanone)-based melting temperatures were between 103° C. and 104° C., while the melting temperatures associated with the lactide-rich-based blend component were observed to be between 146° C. and 148° C.

It is believed that the inventive concepts of this application may be practiced in a variety of ways. Further examples of practice are provided below. Examples 12 through 16 support three categories of practice, Case I, Case II and Case III.

Case I refers to situations in which the first absorbable polymer type is made up of a mixture of a L/G copolymer and a L/G oligomer capped with carboxylic acid groups. Other embodiments of the present invention include situations in which the first absorbable polymer type is made up of a mixture of a polylactide homopolymer and a homo-oligomer capped with carboxylic acid groups.

Case II refers to situations in which the second absorbable polymer type is made up of a mixture of a poly(p-dioxanone) and a p-dioxanone oligomer capped with carboxylic acid groups.

Case III refers to situations in which the first absorbable polymer type is made up of a mixture of a L/G copolymer and a L/G oligomer capped with carboxylic acid groups, and the second absorbable polymer type is made up of a mixture of a poly(p-dioxanone) and a p-dioxanone oligomer capped with carboxylic acid groups. Again, other embodiments of the present invention include situations in which the first absorbable polymer type is made up of a mixture of a polylactide homopolymer and a homo-oligomer capped with carboxylic acid groups.

A summary of these various embodiments is outlined in Table 10 below:

TABLE 10

| Case | Melt Blending | Oligomer Synthesis | Description | | Amount (kg) |
|---|---|---|---|---|---|
| I | Example 14 | Example 12←→ | High MW L/G | Mw = 80,000 | 65 |
| | | | Low MW Capped L/G | Mw = 5,000 | 15 |
| | | | PDS | Mw = 72,000 | 20 |
| | | | Total... | | 100 |
| II | Example 15 | Example 13←→ | High MW L/G | Mw = 80,000 | 80 |
| | | | High MW PDS | Mw = 72,000 | 10 |
| | | | Low MW Capped PDS | Mw = 5,000 | 10 |
| | | | Total... | | 100 |
| III | Example 16 | Example 12←→ | High MW L/G | Mw = 80,000 | 70 |
| | | | Low MW Capped L/G | Mw = 5,000 | 10 |
| | | Example 13←→ | High MW PDS | Mw = 72,000 | 15 |
| | | | Low MW Capped PDS | Mw = 5,000 | 5 |
| | | | Total... | | 100 |

Example 12

Preparation of a Capped Low Molecular Weight L/G Polymer, 85/15 Oligo(L(−)-lactide-co-glycolide)

Into a suitable, conventional 2-gallon stainless steel oil jacketed reactor equipped with agitation, 6,125.4 grams of L(−)-lactide and 870.55 grams of glycolide are added along with 190.1 g of glycolic acid and 1.26 ml of a 0.33M solution of stannous octoate in toluene. The reactor is closed and a purging cycle is initiated, along with agitation at a rotational speed of 7 RPM in an upward direction. The reactor is evacuated to a pressure less than 200 mTorr, and is held at this condition for at least 15 minutes, followed by the introduction of nitrogen gas. The cycle is repeated once again to ensure a dry atmosphere. At the end of the final introduction of nitrogen, the pressure is adjusted to be slightly above one atmosphere. The heating oil temperature is raised to 130° C. at an average heating rate of 120° C./hour. When the batch temperature reaches 120° C., the agitator is stopped and restarted in the downward direction at 7 RPM. The heating oil controller is set at 180° C. at an average heating rate of 60° C. per hour. When the batch reaches 180° C., the reaction is continued for an additional 4 hours and 30 minutes at 7 RPM. The agitator is stopped and 290.2 grams of diglycolic anhydride are added to the reactor. The agitation is continued for 60 minutes at 10 RPM in the downward direction. At the end of the reaction period, the polymer is discharged from the vessel into aluminum trays and stored in a freezer. The polymer is ground and screened through a 3/16" screen.

Example 13

Preparation of a Capped Low MW Poly(p-dioxanone) Oligomer.

Into a suitable, conventional 2-gallon stainless steel oil jacketed reactor equipped with agitation, 6,855 grams of p-dioxanone are added along with 255 g of glycolic acid and 2.00 ml of a 0.33M solution of stannous octoate in toluene. The reactor is closed and a purging cycle is initiated, along with agitation at a rotational speed of 7 RPM in an upward direction. The reactor is evacuated to a pressure less than 200 mTorr, and is held at this condition for at least 15 minutes and is followed by the introduction of nitrogen gas. The cycle is repeated once again to ensure a dry atmosphere. At the end of the final introduction of nitrogen, the pressure is adjusted to be slightly above one atmosphere. The heating oil temperature is raised to 90° C. at an average heating rate of 120° C./hour. When the batch temperature reaches 90° C., the agitator is stopped and is restarted in the downward direction at 7 RPM. The heating oil controller is set at 90° C. at an average heating rate of 60° C. per hour. When the batch reaches 90° C., the reaction is continued for an additional 6 hours at 7 RPM. The agitator is stopped and 398 grams of diglycolic anhydride are added to the reactor. Agitation is continued for 60 minutes at 10 RPM in the downward direction. At the end of the reaction period, the polymer is discharged from the vessel into aluminum trays and is stored in a freezer. The polymer is ground and is screened through a 3/16" screen.

Example 14

Preparation of a Ternary Blend using the Capped L/G Oligomer of Example 12

[This is an example of the Case I Type wherein the Lactide/Glycolide copolymer component possesses a lower molecular weight component wherein at least one component is at least partially end-capped by a carboxylic acid.]

Sixty-five kilograms of pellets or ground material of a lactide/glycolide copolymer having a weight average molecular weight of approximately 80,000 Daltons are dry mixed with 15 kilograms of pellets or ground material of Example 12 having a weight average molecular weight of approximately 5,000 Daltons. This mixture is compounded in a melt-blending operation to result in a blend of a high molecular weight lactide/glycolide copolymer and a lower molecular weight lactide/glycolide that is end-capped with carboxylic acid end groups. This blend is further compounded with 20 kilograms of poly(p-dioxanone) having a weight average molecular weight of approximately 72,000 Daltons so that the poly(p-dioxanone) represents about 20 weight percent of the final blend.

Alternately, one could conduct a single melt compounding operation, in which the feed stock is based on 65 kilograms of a lactide/glycolide copolymer having a weight average molecular weight of approximately 80,000 Daltons, 15 kilograms of pellets or ground material of Example 12 having a weight average molecular weight of approximately 5,000 Daltons, and 20 kilograms poly(p-dioxanone) having a weight average molecular weight of approximately 72,000 Daltons. Thus, the amount of poly(p-dioxanone) represents about 20 weight percent of the final blend.

Example 15

Preparation of a Ternary Blend Using the Capped (p-Dioxanone) Oligomer of Example 13

[This is an example of the Case II Type wherein the poly(p-dioxanone) polymer component possesses a lower molecular weight component wherein at least one component is at least partially end-capped by a carboxylic acid.]

Ten kilograms of pellets or ground material of poly(p-dioxanone) having a weight average molecular weight of approximately 72,000 Daltons are dry mixed with 10 kilograms of pellets or ground material of Example 13 having a weight average molecular weight of approximately 5,000 Daltons. This mixture is compounded in a melt-blending operation to result in a blend of a high molecular weight poly(p-dioxanone) and a lower molecular weight poly(p-dioxanone) that is end-capped with carboxylic acid end groups. This blend is further compounded with 80 kilograms of a lactide/glycolide copolymer having a weight average molecular weight of approximately 80,000 Daltons so that the poly(p-dioxanone) blend represents about 20 weight percent of the final blend.

Alternately, one could conduct a single melt compounding operation, in which the feed stock is based on 80 kilograms of a lactide/glycolide copolymer having a weight average molecular weight of approximately 80,000 Daltons, 10 kilograms of pellets or ground material of Example 13 having a weight average molecular weight of approximately 5,000 Daltons, and 10 kilograms poly(p-dioxanone) having a weight average molecular weight of approximately 72,000 Daltons. Thus the amount of poly(p-dioxanone) represents about 20 weight percent of the final blend.

Example 16

Preparation of a Quaternary Blend Using the Capped L/G Oligomer of Example 12 and the Capped (p-dioxanone) Oligomer of Example 13.
[This is an example of the Case III Type wherein the Lactide/Glycolide copolymer component possesses a lower molecular weight component wherein at least one component is at least partially end-capped by a carboxylic acid, and wherein the poly(p-dioxanone) polymer component possesses a lower molecular weight component wherein at least one component is at least partially end-capped by a carboxylic acid.]

Seventy kilograms of pellets or ground material of a lactide/glycolide copolymer having a weight average molecular weight of approximately 80,000 Daltons are dry mixed with 10 kilograms of pellets or ground material of Example 12 having a weight average molecular weight of approximately 5,000 Daltons. This mixture is compounded in a melt-blending operation to result in a blend of a high molecular weight lactide/glycolide copolymer and a lower molecular weight lactide/glycolide that is end-capped with carboxylic acid end groups.

Fifteen kilograms of pellets or ground material of poly (p-dioxanone) having a weight average molecular weight of approximately 72,000 Daltons are dry mixed with 5 kilograms of pellets or ground material of Example 13 having a weight average molecular weight of approximately 5,000 Daltons. This mixture is compounded in a melt-blending operation to result in a blend of a high molecular weight poly(p-dioxanone) and a lower molecular weight poly(p-dioxanone) that is end-capped with carboxylic acid end groups. The two described blends above are further compounded together so that the poly(p-dioxanone) blend represents about 20 weight percent of the final blend.

Alternately, one could conduct a single melt compounding operation, in which the feed stock is based on 70 kilograms of a lactide/glycolide copolymer having a weight average molecular weight of approximately 80,000 Daltons, 10 kilograms of pellets or ground material of Example 12 having a weight average molecular weight of approximately 5,000 Daltons, 15 kilograms poly(p-dioxanone) having a weight average molecular weight of approximately 72,000 Daltons and 5 kilograms of Example 13. Thus the amount of poly(p-dioxanone) represents about 20 weight percent of the final blend.

It should be clear to one having ordinary skill in the art that similar blends differing in composition can be made in like manner.

Example 17

Calculating the Minimum Weight Percent of Poly(p-Dioxanone) in the Invention when the Lactide-Rich Polymer Comprises Capped Oligomer In the case of the lactide-based polymer comprising capped oligomer, the weight percent of the poly(p-dioxanone) can be calculated using the equation found below.

Weight Percent Poly(p-dioxanone)=$(215.6212/\text{Mole Percent Polymerized Lactide})^{2.7027}$−3.6273

Wherein the Lactide-Based Polymer Comprises Capped Oligomer

For example, when the composition of the lactide-rich lactide-co-glycolide copolymer comprising capped oligomer was 82/8 (on a mole basis), the minimum weight percent of poly(p-dioxanone) [either further comprising capped oligomer or not] in the blend was calculated to be 10.0 percent and the maximum amount was 50. Likewise, if the composition of the bimodal lactide-co-glycolide copolymer was 86/14 (on a mole basis), the minimum weight percent of unimodal or bimodal poly(p-dioxanone) in the blend was calculated to be 8.4 percent and the maximum amount was 50. Table 11 contains a chart of the range of poly(p-dioxanone), expressed as minimum and maximum weight percent, in the blend of the subject invention. It should be noted that the poly(p-dioxanone) in this case may comprise capped oligomer or not.

TABLE 11

Inventive Blend Compositions of Lactide-Rich, Lactide/Glycolide (Co) Polymer Comprising Capped Oligomer and Poly(p-Dioxanone)

| Mole Percent of Polymerized Lactide in the Lactide-Based (Co)Polymer Comprising Capped Oligomer | Minimum Weight Percent Poly(p-dioxanone) Polymer in the Blend | Maximum Weight Percent Poly(p-dioxanone) Polymer in the Blend |
|---|---|---|
| 100 | 4.4 | 50 |
| 99 | 4.6 | 50 |
| 98 | 4.8 | 50 |
| 97 | 5.0 | 50 |
| 96 | 5.3 | 50 |
| 95 | 5.5 | 50 |
| 94 | 5.8 | 50 |
| 93 | 6.1 | 50 |
| 92 | 6.4 | 50 |
| 91 | 6.7 | 50 |
| 90 | 7.0 | 50 |
| 89 | 7.3 | 50 |
| 88 | 7.6 | 50 |
| 87 | 8.0 | 50 |
| 86 | 8.4 | 50 |
| 85 | 8.8 | 50 |
| 84 | 9.2 | 50 |
| 83 | 9.6 | 50 |
| 82 | 10.0 | 50 |
| 81 | 10.5 | 50 |
| 80 | 11.0 | 50 |
| 79 | 11.5 | 50 |
| 78 | 12.0 | 50 |
| 77 | 12.5 | 50 |
| 76 | 13.1 | 50 |

TABLE 11-continued

Inventive Blend Compositions of Lactide-Rich, Lactide/Glycolide (Co)
Polymer Comprising Capped Oligomer and Poly(p-Dioxanone)

| Mole Percent of Polymerized Lactide in the Lactide-Based (Co)Polymer Comprising Capped Oligomer | Minimum Weight Percent Poly(p-dioxanone) Polymer in the Blend | Maximum Weight Percent Poly(p-dioxanone) Polymer in the Blend |
|---|---|---|
| 75 | 13.7 | 50 |
| 74 | 14.4 | 50 |
| 73 | 15.0 | 50 |
| 72 | 15.8 | 50 |
| 71 | 16.5 | 50 |
| 70 | 17.3 | 50 |

Example 18

Calculating the Minimum Weight Percent of Poly(p-Dioxanone) Comprising Capped Oligomer in the Invention when the Lactide-Rich Polymer does not Comprise Capped Oligomer In the case of the lactide-based polymer not comprising capped oligomer, the weight percent of the poly(p-dioxanone) comprising capped oligomer can be calculated using the equation found below.

Weight Percent Poly(p-dioxanone) Comprising Capped Oligomer=$(215.6212/\text{Mole Percent Polymerized Lactide})^{2.7027}$ Wherein the Lactide-Based Polymer Does Not Comprise Capped Oligomer For example, when the composition of the lactide-rich lactide-co-glycolide copolymer does not comprise capped oligomer was 82/8 (on a mole basis), the minimum weight percent of poly(p-dioxanone) comprising capped oligomer in the blend was calculated to be 13.6 percent and the maximum amount was 50. Likewise, if the composition of the lactide-co-glycolide copolymer not comprising capped oligomer was 86/14 (on a mole basis), the minimum weight percent of poly(p-dioxanone) comprising capped oligomer in the blend was calculated to be 120 percent and the maximum amount was 50. Table 12 contains a chart of the range of poly(p-dioxanone) comprising capped oligomer, expressed as minimum and maximum weight percent, in the blend of the subject invention.

TABLE 12

Inventive Blend Compositions of Lactide-Rich, Lactide/Glycolide
(Co)Polymer Not Comprising Capped Oligomer and
Poly(p-Dioxanone) Comprising Capped Oligomer

| Mole Percent of Polymerized Lactide in the Lactide-Based (Co)Polymer Not Comprising Capped Oligomer | Minimum Weight Percent Poly(p-dioxanone) Comprising Capped Oligomer in the Blend, | Maximum Weight Percent Poly(p-dioxanone) Comprising Capped Oligomer in the Blend |
|---|---|---|
| 100 | 8.0 | 50 |
| 99 | 8.2 | 50 |
| 98 | 8.4 | 50 |
| 97 | 8.7 | 50 |
| 96 | 8.9 | 50 |
| 95 | 9.2 | 50 |
| 94 | 9.4 | 50 |
| 93 | 9.7 | 50 |
| 92 | 10.0 | 50 |
| 91 | 10.3 | 50 |
| 90 | 10.6 | 50 |
| 89 | 10.9 | 50 |
| 88 | 11.3 | 50 |
| 87 | 11.6 | 50 |
| 86 | 12.0 | 50 |
| 85 | 12.4 | 50 |
| 84 | 12.8 | 50 |
| 83 | 13.2 | 50 |
| 82 | 13.6 | 50 |
| 81 | 14.1 | 50 |
| 80 | 14.6 | 50 |
| 79 | 15.1 | 50 |
| 78 | 15.6 | 50 |
| 77 | 16.2 | 50 |
| 76 | 16.7 | 50 |
| 75 | 17.4 | 50 |
| 74 | 18.0 | 50 |
| 73 | 18.7 | 50 |
| 72 | 19.4 | 50 |
| 71 | 20.1 | 50 |
| 70 | 20.9 | 50 |

Although this invention has been shown and described with respect to detailed embodiments thereof, it will be understood by those skilled in the art that various changes in form and detail thereof may be made without departing from the spirit and scope of the claimed invention. It will be understood that the embodiments described herein are merely exemplary and that a person skilled in the art may make many variations and modifications, including but not limited to those discussed hereinabove, without departing from the spirit and scope of the present invention. All such variations and modifications are intended to be included within the scope of the present invention.

We claim:
1. An absorbable medical device, comprising:
an absorbable polymer blend, said blend comprising:
a first absorbable polymer type, the first absorbable polymer type comprising at least 50 weight percent of the blend and comprising about 100 mole percent to about 70 mole percent polymerized lactide and about 0 mole percent to about 30 mole percent polymerized glycolide; and,
a second absorbable polymer type, the second polymer type comprising poly(p-dioxanone),
wherein the maximum weight percent of poly(p-dioxanone) in the blend is 50 weight percent and the minimum weight percent of poly(p-dioxanone) in the blend is 5 weight percent, wherein further the first absorbable polymer type and the second absorbable polymer type comprise a polymeric component and an oligomeric component, wherein the polymeric component has a higher weight average molecular weight than the oligomeric component, wherein the oligomeric component has a weight average molecular weight of about 1,400 to about 5,200 Daltons, and wherein at least one of said oligomeric components is at least partially end-capped by a carboxylic acid.
2. The blend of claim 1, wherein the first absorbable polymer type comprises a polymer selected from the group consisting of poly(L(−)-lactide), poly(D(+)-lactide), poly(L(−)-lactide)/poly(D(+)-lactide) stereocomplex, and a lactide-rich lactide/glycolide copolymer.

3. The absorbable polymer blend of claim 1 wherein the absorbable polymer blend has a weight average molecular weight of at least 35,000 Daltons.

4. The absorbable polymer blend of claim 1, wherein the first absorbable polymer type comprises a carboxylic acid end-capped oligomer.

5. The absorbable polymer blend of claim 4, wherein the second absorbable polymer type does not comprise carboxylic acid end-capped oligomer.

6. The blend of claim 4, wherein the first absorbable polymer type comprises an amount of a polylactide or lactide-rich lactide/glycolide copolymer having a first weight average molecular weight between about 42,000 Daltons to about 175,000 Daltons; and, a second amount of a polylactide or lactide-rich lactide/glycolide copolymer having a second weight average molecular weight between about 1,400 Daltons to about 5,200 Daltons, wherein a blend of the first and second amounts of the first absorbable polymer type is formed in a ratio of between about 50/50 to 99/1 weight/weight percent.

7. The absorbable polymer blend of claim 1, wherein the first absorbable polymer type does not comprise a carboxylic acid end-capped oligomer.

8. The blend of claim 7, wherein the first absorbable polymer type comprises a polymer selected from the group consisting of poly(L(−)-lactide), poly(D(+)-lactide), poly(L(−)-lactide)/poly(D(+)-lactide) stereocomplex, and a lactide-rich lactide/glycolide copolymer, said blend having a first weight average molecular weight between about 42,000 Daltons to about 175,000 Daltons.

9. The absorbable polymer blend of claim 7, wherein the second absorbable polymer comprises a carboxylic acid end-capped oligomer.

10. The blend of claim 9, wherein the second absorbable polymer type comprises a first amount of a poly(p-dioxanone) polymer having a first weight average molecular weight between about 42,000 Daltons to about 175,000 Daltons; and, a second amount of a poly(p-dioxanone) polymer having a second weight average molecular weight between about 1,400 Daltons to about 24,000 Daltons, and wherein a blend of the first and second amounts of the second absorbable polymer type is formed in a ratio of between 50/50 to 99/1 weight/weight percent.

11. The absorbable polymer blend of claim 1, wherein the first and second absorbable polymer types each comprise a carboxylic acid end-capped oligomer.

12. The blend of claim 11, wherein the first absorbable polymer type comprises a first amount of a polylactide or lactide-rich lactide/glycolide copolymer having first a weight average molecular weight between about 42,000 Daltons to about 175,000 Daltons, and a second amount of a polylactide or lactide-rich lactide/glycolide copolymer having a second weight average molecular weight between about 1,400 Daltons to about 24,000 Daltons, wherein a blend of the first and second amounts of the first absorbable polymer types is formed in a ratio of between about 50/50 to 99/1 weight/weight percent; and, wherein the second absorbable polymer type comprises a first amount of a poly(p-dioxanone) polymer having a first weight average molecular weight between about 42,000 Daltons to about 175,000 Daltons and a second amount of a poly(p-dioxanone) polymer having a second weight average molecular weight between about 1,400 Daltons to about 24,000 Daltons, and wherein a blend of the first and second amounts of each absorbable poly(p-dioxanone) polymer is formed in a ratio of between about 50/50 to 99/1 weight/weight percent.

13. An absorbable polymer blend, comprising:
a first absorbable polymer type, the first absorbable polymer type comprising at least 50 weight percent of the blend and comprising about 100 mole percent to about 70 mole percent polymerized lactide and about 0 mole percent to about 30 mole percent polymerized glycolide; and,
a second absorbable polymer type, the second absorbable polymer type comprising poly(p-dioxanone),
wherein the maximum weight percent of poly(p-dioxanone) in the blend is 50 weight percent, wherein further the first absorbable polymer type or the second absorbable polymer type or the first absorbable polymer type and the second absorbable polymer type comprise a polymeric component and an oligomeric component, wherein the polymeric component has a higher weight average molecular weight than the oligomer component and wherein at least one of said components is at least partially end-capped by a carboxylic acid,
wherein further the minimum weight percent of poly(p-dioxanone) in the blend depends upon the molar amount of polymerized lactide in the first absorbable polymer type and is calculated by the expression:

$$\text{Weight Percent Poly(p-dioxanone)} = (215.6212/\text{Mole Percent Polymerized Lactide})^{2.7027}$$

when the first absorbable polymer type does not comprise carboxylic acid capped oligomer and the poly(p-dioxanone) comprises carboxylic acid capped oligomer,
and wherein the polymer blend provides dimensional stability to a manufactured article.

14. An absorbable medical device, comprising:
an absorbable polymer blend, said blend comprising:
a first absorbable polymer type, the first absorbable polymer type comprising at least 50 weight percent of the blend and comprising about 100 mole percent to about 70 mole percent polymerized lactide and about 0 mole percent to about 30 mole percent polymerized glycolide; and,
a second absorbable polymer type, the second absorbable polymer type comprising poly(p-dioxanone),
wherein the maximum weight percent of poly(p-dioxanone) in the blend is 50 weight, wherein further the first absorbable polymer type and the second absorbable polymer type comprise a polymeric component and an oligomeric component, wherein the polymeric component has a higher weight average molecular weight than the oligomer component, wherein the oligomeric component has a weight average molecular weight of about 1,400 to about 5,200 Daltons, and wherein at least one of said oligomeric components is at least partially end-capped by a carboxylic acid,
wherein the minimum weight percent of poly(p-dioxanone) in the blend depends upon the molar amount of polymerized lactide in the first absorbable polymer type and is calculated by the expression:

$$\text{Weight Percent Poly(p-dioxanone)} = (215.6212/\text{Mole Percent Polymerized Lactide})^{2.7027} - 3.6273$$

when the oligomeric component of the first absorbable polymer type comprises carboxylic acid capped oligomer and the oligomeric component of the poly(p-dioxanone) either comprises or does not comprise carboxylic acid capped oligomer, and wherein the polymer blend provides dimensional stability to a manufactured article.

15. A medical device comprising the absorbable polymer blend of claim 13.

16. A method of manufacturing a medical device, comprising the step of processing the absorbable polymer blend of claim 1 into a medical device.

17. A method of manufacturing a medical device, comprising the step of processing the absorbable polymer blend of claim 13 into a medical device.

18. A method of manufacturing a medical device, comprising the step of processing the absorbable polymer blend of claim 14 into a medical device.

19. The method of claim 16, wherein the method comprises melt processing.

20. The method of claim 17, wherein the method comprises melt processing.

21. The method of claim 18, wherein the method comprises melt processing.

22. The blend of claim 6 wherein the first and second amounts of the first absorbable polymer type are formed in a ratio of between about 78/22 to about 88/12 weight/weight percent.

23. The blend of claim 10 wherein the first and second amounts of the second absorbable polymer type are formed in a ratio of between about 78/22 to about 88/12 weight/weight percent.

24. The blend of claim 12 wherein the first and second amounts of the first absorbable polymer type are formed in a ratio of between about 78/22 to about 88/12 weight/weight percent and the second absorbable polymer type is formed in a ratio of between about 78/22 to about 88/12 weight/weight percent.

* * * * *